US012740743B2

(12) United States Patent
Garcia et al.

(10) Patent No.: US 12,740,743 B2
(45) Date of Patent: Sep. 22, 2026

(54) SYSTEM, METHOD AND COMPUTER-ACCESSIBLE MEDIUM FOR ANESTHESIA MONITORING USING ELECTROENCEPHALOGRAPHIC MONITORING

(71) Applicants: THE TRUSTEES OF COLUMBIA UNIVERSITY IN THE CITY OF NEW YORK, New York, NY (US); TECHNISCHE UNIVERSITAT MUNCHEN, Munich (DE)

(72) Inventors: Paul Garcia, Cortlandt Manor, NY (US); Matthias Kreuzer, Munich (DE)

(73) Assignees: THE TRUSTEES OF COLUMBIA UNIVERSITY IN THE CITY OF NEW YORK, New York, NY (US); TECHNISCHE UNIVERSITAT MUNCHEN, Munich (DE)

( * ) Notice: Subject to any disclaimer, the term of this patent is extended or adjusted under 35 U.S.C. 154(b) by 992 days.

(21) Appl. No.: 17/717,708

(22) Filed: Apr. 11, 2022

(65) Prior Publication Data

US 2022/0246310 A1 Aug. 4, 2022

Related U.S. Application Data

(63) Continuation of application No. PCT/US2020/055414, filed on Oct. 13, 2020.

(Continued)

(51) Int. Cl.

*A61B 5/00* (2006.01)
*A61B 5/31* (2021.01)

(Continued)

(52) U.S. Cl.

CPC .............. *A61B 5/4821* (2013.01); *A61B 5/31* (2021.01); *A61B 5/372* (2021.01); *A61B 5/374* (2021.01);

(Continued)

(58) Field of Classification Search

CPC ........... A61B 5/31; A61B 5/372; A61B 5/374; A61B 5/369

See application file for complete search history.

(56) References Cited

U.S. PATENT DOCUMENTS

| | | | |
|---|---|---|---|
| 6,801,803 | B2 | 10/2004 | Viertiö-Oja et al. |
| 7,920,914 | B2 | 4/2011 | Shieh et al. |

(Continued)

OTHER PUBLICATIONS

European Search Report mailed on Aug. 31, 2023 for European Patent Application No. 20873935.9.

(Continued)

*Primary Examiner* — May A Abouelela
*Assistant Examiner* — Yasmeen S Warsi
(74) *Attorney, Agent, or Firm* — Hunton Andrews Kurth LLP

(57) ABSTRACT

An exemplary system, method, and computer-accessible medium for determining an effect of an age of a patient(s) during an administration of a compound can include, for example, receiving electroencephalographic (EEG) information for the patient(s) during the administration of the compound to the patient(s); and determining the effect of the age of the patient(s) based on the EEG information. A bispectral index of the at least one patient during the administration of the compound, or an entropy of the at least one patient during the administration of the compound can be received, and the effect of the age of the patient(s) can be determined based on the bispectral index, or the entropy. The compound can include an anesthesia. The anesthesia can include (i) sevoflurane, (ii) isoflurane, (iii) dexmedetomi- (Continued)

dine, (iv) propofol, (v) etomidate, (vi) desflurane, or (vii) a combination of ketamine and nitrous oxide.

19 Claims, 14 Drawing Sheets

Related U.S. Application Data

(60) Provisional application No. 62/960,947, filed on Jan. 14, 2020, provisional application No. 62/914,183, filed on Oct. 11, 2019.

(51) Int. Cl.

| | |
|---|---|
| ***A61B 5/372*** | (2021.01) |
| ***A61B 5/374*** | (2021.01) |
| ***A61K 31/05*** | (2006.01) |
| ***A61K 31/08*** | (2006.01) |
| ***G16H 10/60*** | (2018.01) |
| ***G16H 50/30*** | (2018.01) |
| ***G16H 50/70*** | (2018.01) |

(52) U.S. Cl.

CPC .............. *A61K 31/05* (2013.01); *A61K 31/08* (2013.01); *G16H 10/60* (2018.01); *G16H 50/30* (2018.01); *G16H 50/70* (2018.01)

(56) References Cited

U.S. PATENT DOCUMENTS

| | | | | |
|---|---|---|---|---|
| 10,602,978 | B2 | 3/2020 | Brown et al. | |
| 2008/0317672 | A1* | 12/2008 | Viertio-Oja .......... | A61B 5/4821 424/9.1 |
| 2009/0275853 | A1 | 11/2009 | Sarkela | |
| 2009/0292180 | A1* | 11/2009 | Mirow ................... | G16H 10/20 600/300 |
| 2014/0187973 | A1 | 7/2014 | Brown et al. | |
| 2015/0080754 | A1* | 3/2015 | Purdon ................. | A61B 5/369 600/544 |
| 2016/0029946 | A1 | 2/2016 | Simon et al. | |
| 2017/0181693 | A1 | 6/2017 | Cha et al. | |
| 2017/0231556 | A1 | 8/2017 | Akeju et al. | |

OTHER PUBLICATIONS

Notification Concerning Transmittal of International Preliminary Report on Patentability (Chapter I of the Patent Cooperation Treaty) mailed on Apr. 21, 2022 for International Patent Application No. PCT/US2020/055414.

Delafuente JC: The silver tsunami is coming: will pharmacy be swept away with the tide? Am. J. Pharm. Educ. 2009; 73: 1.

Etzioni DA, Liu JH, Mareggard MA, Ko CY: The aging population and its impact on the surgery workforce. Ann. Surg. 2003; 238: 170.

Fritz BA, Kalarickal PL, Maybrier HR, Muench MR, Dearth D, Chen Y, Escalier KE, Ben Abdallah A, Lin N, Avidan MS: Intraoperative Electroencephalogram Suppression Predicts Postoperative Delirium. Anesth. Analg. 2016; 122: 234-42.

Radtke F, Franck M, Hagemann L, Seeling M, Wernecke K, Spies C: Risk factors for inadequate emergence after anesthesia: emergence delirium and hypoactive emergence. Minerva Anestesiol. 2010; 76: 394-403.

Watson PL, Shintani AK, Tyson R, Pandharipande PP, Pun BT, Ely EW: Presence of electroencephalogram burst suppression in sedated, critically ill patients is associated with increased mortality. Crit. Care Med. 2008; 36: 3171-7.

Radtke F, Franck M, Lendner J, Krüger S, Wernecke K, Spies C: Monitoring depth of anaesthesia in a randomized trial decreases the rate of postoperative delirium but not postoperative cognitive dysfunction. Br J Anaesth 2013; 110: i98-i105.

Wildes TS, et al. "Effect of Electroencephalography-Guided Anesthetic Administration on Postoperative Delirium Among Older Adults Undergoing Major Surgery: The ENGAGES Randomized Clinical Trial" JAMA 2019; 321: 473-483.

Schultz A, Grouven U, Zander I, Beger FA, Siedenberg M, Schultz B: Age-related effects in the EEG during propofol anesthesia. Acta Anaesthesiol Scand 2004; 48: 27-34.

Purdon P, Pavone K, Akeju O, Smith A, Sampson A, Lee J, Zhou D, Solt K, Brown E: The Ageing Brain: Age-dependent changes in the electroencephalogram during propofol and sevoflurane general anesthesia. Br J Anaesth 2015; 115: i46-i57.

Giattino C, Gardner J, Sbahi F, Roberts K, Cooter M, Moretti E, Browndyke J, Mathew J, Woldorff M, Berger M: Intraoperative Frontal Alpha-Band Power Correlates with Preoperative Neurocognitive Function in Older Adults. Front. Syst. Neurosci. 2017; 11.

Polich J: EEG and ERP assessment of normal aging. Electroencephalography and Clinical Neurophysiology/Evoked Potentials Section 1997; 104: 244-256.

Carrier J, Land S, Buysse DJ, Kupfer DJ, Monk TH: The effects of age and gender on sleep EEG power spectral density in the middle years of life (ages 20-60 years old). Psychophysiology 2001; 38: 232-242.

Bandt C, Pompe B: Permutation Entropy: A Natural Complexity Measure for Time Series. Phys. Rev. Lett. 2002; 88: 174102.

Pincus SM: Approximate entropy as a measure of system complexity. Proc. Natl. Acad. Sci. U. S. A 1991; 88: 2297-2301.

Olofsen E, Sleigh JW, Dahan A: Permutation entropy of the electroencephalogram: a measure of anaesthetic drug effect. Br J Anaesth 2008; 101: 810-21.

Jordan D, Stockmanns G, Kochs EF, Pilge S, Schneider G: Electroencephalographic Order Pattern Analysis for the Separation of Consciousness and Unconsciousness: An Analysis of Approximate Entropy, Permutation Entropy, Recurrence Rate, and Phase Coupling of Order Recurrence Plots. Anesthesiology 2008; 109: 1014-1022.

Schneider G, Jordan D, Schwarz G, Bischoff P, Kalkman CJ, Kuppe H, Rundshagen I, Omerovic A, Kreuzer M, Stockmanns G, Kochs EF: Monitoring depth of anesthesia utilizing a combination of electroencephalographic and standard measures. Anesthesiology 2014; 120: 819-28.

Rampil IJ: A Primer for EEG Signal Processing in Anesthesia. Anesthesiology 1998; 89: 980-1002.

Viertio-Oja H, et al. "Description of the Entropy algorithm as applied in the Datex-Ohmeda S/5 Entropy Module". Acta Anaesthesiol Scand 2004; 48: 154-61.

Hight D, Voss LJ, Garcia PS, Sleigh J: Changes in Alpha Frequency and Power of the Electroencephalogram during Volatile-Based General Anesthesia. Front. Syst. Neurosci. 2017.

McKay ID, Voss LJ, Sleigh JW, Barnard JP, Johannsen EK: Pharmacokinetic-pharmacodynamic modeling the hypnotic effect of sevoflurane using the spectral entropy of the electroencephalogram. Anesth. Analg. 2006; 102: 91-97.

Mapleson W: Effect of age on MAC in humans: a meta-analysis. Br J Anaesth 1996; 76: 179-185.

Mazoit JX, Butscher K, Samii K: Morphine in postoperative patients: pharmacokinetics and pharmacodynamics of metabolites. Anesth. Analg. 2007; 105: 70-78.

Shafer SL, Varvel JR: Pharmacokinetics, pharmacodynamics, and rational opioid selection. Anesthesiology 1991; 74: 53-63.

Wiczling P, et al. "Pharmacokinetics and pharmacodynamics of propofol in patients undergoing abdominal aortic surgery". Pharmacol. Rep. 2012; 64: 113-122.

Haller M, Donoghue T, Peterson E, Varma P, Sebastian P, Gao R, Noto T, Knight RT, Shestyuk A, Voytek B: Parameterizing neural power spectra. bioRxiv 2018: 299859.

Bruhn J, Ropcke H, Hoeft A: Approximate Entropy as an Electroencephalographic Measure of Anesthetic Drug Effect during Desflurane Anesthesia. Anesthesiology 2000; 92: 715-726.

Shannon C: A Mathematical Theory of Communication. Bell Syst. Tech. J 1948; 27: (379-423):623-56.

Kreuzer M: EEG Based Monitoring of General Anesthesia: Taking the Next Steps. Front. Comput. Neurosci. 2017; 11: 56.

Goldberger A, Amaral L, Glass L, Hausdorff J, Ivanov P, Mark R, Mietus J, Moody G, Peng C, Stanley H: PhysioBank, PhysioToolkit,

(56) References Cited

OTHER PUBLICATIONS and PhysioNet: Components of a New Research Resource for Complex Physiologic Signals. Circulation 2000; 101: e215-e220.
Schneider G, Schöniger S, Kochs E: Does bispectral analysis add anything but complexity? BIS sub-components may be superior to BIS for detection of awareness. Br J Anaesth 2004; 93: 596-597.
Hentschke H, Stüttgen MC: Computation of measures of effect size for neuroscience data sets. Eur. J. Neurosci. 2011; 34: 1887-1894.
Akeju O, Westover MB, Pavone KJ, Sampson AL, Hartnack KE, Brown EN, Purdon PL: Effects of sevoflurane and propofol on frontal electroencephalogram power and coherence. Anesthesiology 2014; 121: 990-998.
Raz N, Lindenberger U, Rodrigue KM, Kennedy KM, Head D, Williamson A, Dahle C, Gerstorf D, Acker JD: Regional brain changes in aging healthy adults: General trends, individual differences and modifiers. Cereb. Cortex 2005; 15: 1676-1689.
Salat DH, Buckner RL, Snyder AZ, Greve DN, Desikan RSR, Busa E, Morris JC, Dale AM, Fischl B: Thinning of the cerebral cortex in aging. Cereb. Cortex 2004; 14: 721-730.
Fjell AM, Walhovd KB, Fennema-Notestine C, McEvoy LK, Hagler DJ, Holland D, Brewer JB, Dale AM: One-Year Brain Atrophy Evident in Healthy Aging. J. Neurosci. 2009; 29: 15223-15231.
Fjell AM, Westlye LT, Amlien I, Espeseth T, Reinvang I, Raz N, Agartz I, Salat DH, Greve DN, Fischl B: High consistency of regional cortical thinning in aging across multiple samples. Cereb. Cortex 2009: bhn232.
Thompson PM, et al. "Tracking Alzheimer's disease." Ann. N. Y. Acad. Sci. 2007; 1097: 183-214.
Voytek B, Kramer MA, Case J, Lepage KQ, Tempesta ZR, Knight RT, Gazzaley A: Age-Related Changes in 1/f Neural Electrophysiological Noise. J Neurosci 2015; 35: 13257-65.
Chinoy ED, Frey DJ, Kaslovsky DN, Meyer FG, Wright KP: Age-related changes in slow wave activity rise time and NREM sleep EEG with and without zolpidem in healthy young and older adults. Sleep Med. 2014; 15: 1037-1045.
Bruce EN, Bruce MC, Vennelaganti S: Sample entropy tracks changes in EEG power spectrum with sleep state and aging. J. Clin. Neurophysiol. 2009; 26: 257.
Dave S, Brothers TA, Swaab TY: 1/f neural noise and electrophysiological indices of contextual prediction in aging. Brain Research 2018; 1691: 34-43.
Kaiser AK, Doppelmayr M, Iglseder B: EEG beta 2 power as surrogate marker for memory impairment: a pilot study. Int. Psychogeriatr. 2017; 29: 1515-1523.
Vysata O, Kukal J, Prochazka A, Pazdera L, Simko J, Valis M: Age-related changes in EEG coherence. Neurol. Neurochir. Pol. 2014; 48: 35-38.
Hammerer D, Li SC, Volkle M, Muller V, Lindenberger U: A lifespan comparison of the reliability, test-retest stability, and signal-to-noise ratio of event-related potentials assessed during performance monitoring. Psychophysiology 2013; 50: 111-23.
Keller K, Mangold T, Stolz I, Werner J: Permutation Entropy: New Ideas and Challenges. Entropy 2017; 19: 134.
Brown EN, Lydic R, Schiff ND: General Anesthesia, Sleep, and Coma. N. Engl. J. Med. 2010; 363: 2638-2650.
Shumbayawonda E, Fernández A, Hughes MP, Abásolo D: Permutation Entropy for the Characterisation of Brain Activity Recorded with Magnetoencephalograms in Healthy Ageing. Entropy 2017; 19: 141.
Berger S, Schneider G, Kochs EF, Jordan D: Permutation Entropy: Too Complex a Measure for EEG Time Series? Entropy 2017; 19: 692.
John ER, Prichep LS: The Anesthetic Cascade: A Theory of How Anesthesia Suppresses Consciousness. Anesthesiology 2005; 102: 447-471.
Kreuzer M, Whalin MK, Hesse SD, Riso MA, Garcia PS: Anesthetic Management of a Patient With Multiple Previous Episodes of Postanesthesia Care Unit Delirium: A Case Report. A&A Case Reports 2017; 8: 311-315.
Chander D, Garcia PS, MacColl JN, Illing S, Sleigh JW: Electroencephalographic variation during end maintenance and emergence from surgical anesthesia. PloS one 2014; 9: e106291.
Hesse S, Kreuzer M, Hight D, Gaskell A, Devari P, Singh D, Taylor N, Whalin M, Lee S, Sleigh J: Association of electroencephalogram trajectories during emergence from anesthesia with delirium in the post-anesthesia care unit: an early sign of postoperative complications. Br J Anaesth 2019; 122: 622-634.
Bassett DS, Bullmore ET, Meyer-Lindenberg A, Apud JA, Weinberger DR, Coppola R: Cognitive fitness of cost-efficient brain functional networks. Proc. Natl. Acad. Sci. U. S. A 2009; 106: 11747-11752.
Crowley K, Trinder J, Kim Y, Carrington M, Colrain IM: The effects of normal aging on sleep spindle and K-complex production. Clin. Neurophysiol. 2002; 113: 1615-1622.
Frantzidis CA, et al. "What are the symbols of Alzheimer? A permutation entropy based symbolic analysis for the detection of early changes of the electroencephalographic complexity due to mild Alzheimer," Bioinformatics & Bioengineering (BIBE), 2012 IEEE 12th International Conference on, IEEE, 2012, pp. 282-287.
Pilge S, Zanner R, Schneider G, Blum J, Kreuzer M, Kochs E: Time Delay of Index Calculation: Analysis of Cerebral State, Bispectral, and Narcotrend Indices. Anesthesiology 2006; 104: 488-494.
Zanner R, Pilge S, Kochs EF, Kreuzer M, Schneider G: Time delay of electroencephalogram index calculation: analysis of cerebral state, bispectral, and Narcotrend indices using perioperatively recorded electroencephalographic signals. Br J Anaesth 2009; 103: 394-399.
Ni K, Cooter M, Gupta DK, Thomas J, Hopkins TJ, Miller TE, James ML, Kertai MD, Berger M: Paradox of age: older patients receive higher age-adjusted minimum alveolar concentration fractions of volatile anaesthetics yet display higher bispectral index values. Br J Anaesth 2019; 123: 288-297.
Prichep L, Gugino L, John E, Chabot R, Howard B, Merkin H, Tom M, Wolter S, Rausch L, Kox W: The Patient State Index as an indicator of the level of hypnosis under general anaesthesia. Br J Anaesth 2004; 92: 393-399.
Lysakowski C, Elia N, Czarnetzki C, Dumont L, Haller G, Combescure C, Tramer MR: Bispectral and spectral entropy indices at propofol-induced loss of consciousness in young and elderly patients. Br J Anaesth 2009; 103: 387-93.
Dundee J, Robinson FP, McCollum J, Patterson C: Sensitivity to propofol in the elderly. Anaesthesia 1986; 41: 482-485.
Teplan M: Fundamentals of EEG measurement. Meas. Sci. Rev. 2002; 2: 1-11.
Yi GS, et al. "Complexity of resting-state EEG activity in the patients with early-stage Parkinson's disease" Cognitive Neurodynamics, vol. 11 / Issue 2, Oct. 20, 2016.
Mamashi F, et al. "Permutation Statistics for Connectivity Analysis between Regions of Interest in EEG and MEG Data" Scientific Reports, vol. 9, 7942, pp. 1-10, May 28, 2019.
Racz FS, et al. "Multifractal and entropy analysis of resting-state electroencephalography reveals spatial organization in local dynamic functional connectivity" Scientific Reports, vol. 9, 13474, pp. 1-15, Sep. 17, 2019.
Grandy TH, et al. "On the estimation of brain signal entropy from sparse neuroimaging data" Scientific Reports, vol. 6, 23073, Mar. 29, 2016.
Purdon PL, et al. "The Ageing Brain: Agedependent changes in the electroencephalogram during propofol and sevoflurane general anaesthesia" British Journal of Anaesthesia, vol. 115 / Issue 1, pp. 146-157, Jul. 14, 2015.
International Search Report and Written Opinion for International Patent Application No. PCT/US2020/055414 mailed on Feb. 2, 2021.
N. Nicolaou, et al., "Entropy measures for discrimination of 'awake' Vs 'anaesthetized' state in recovery from general anesthesia," Conf Proc IEEE Eng Med Biol Soc 2011; 2011: 2598-601 (Abstract Only).
D. Jordan D, et al., "Is Detection of Different Anesthetic Levels Related to Nonlinearity of the Electroencephalogram?," 4th European Conference of the International Federation for Medical and Biological Engineering. Edited by Sloten J, Verdonck P, Nyssen M, Haueisen J, Springer Berlin Heidelberg, 2009, pp. 335-339.

(56) References Cited

OTHER PUBLICATIONS

Hoekema, et al., "Measurement of the conductivity of skull, temporarily removed during epilepsy surgery," Brain Topogr. 2003; 16: 29-38.

Bedard, et al., "Does the 1/f frequency scaling of brain signals reflect self-organized critical states?," Phys. Rev. Lett. 2006; 97: 118102.

* cited by examiner sevoflurane concentration
y = 1.08-.004x (slope coefficient: p<0.001; R²; 0.17).
MAC sevoflurane
Age [yr]
605
610 age adjusted sevoflurane concentration
y = 1.08-.004x (slope coefficient: p<0.001; R²; 0.17).
MAC sevoflurane
Age [yr]
605
610 propofol effect site concentration
y = 1.08-.004x (slope coefficient: p<0.001; R²; 0.17).
Propofol [ µl/mg]
Age [yr]
605
610 opioids
y = 2.07-0.005x (slope coefficient; p=0.319; R2: 0.006).
fentanyl equivalents
Age [yr]
605
610 relative theta pwr
0.4
0.3
0.2
0.1
910
0
20
40
60
80
100
Age [yr]
905
0.3
0.2
0.1
0 y=0.411-0.001X (slope 95% ci: [ -0.001 - 0.0001]; p=0.029; R²=0.03)
ApEn (delta)
1010
1005
Age [yr]
Y25
O25

ApEn (theta)
1010
1005
Age [yr]
Y25
O25

PeEn (delta)
1010
1005
Age [yr]
Y25
O25

PeEn (delta)
1010
1005
Age [yr]
Y25
O25

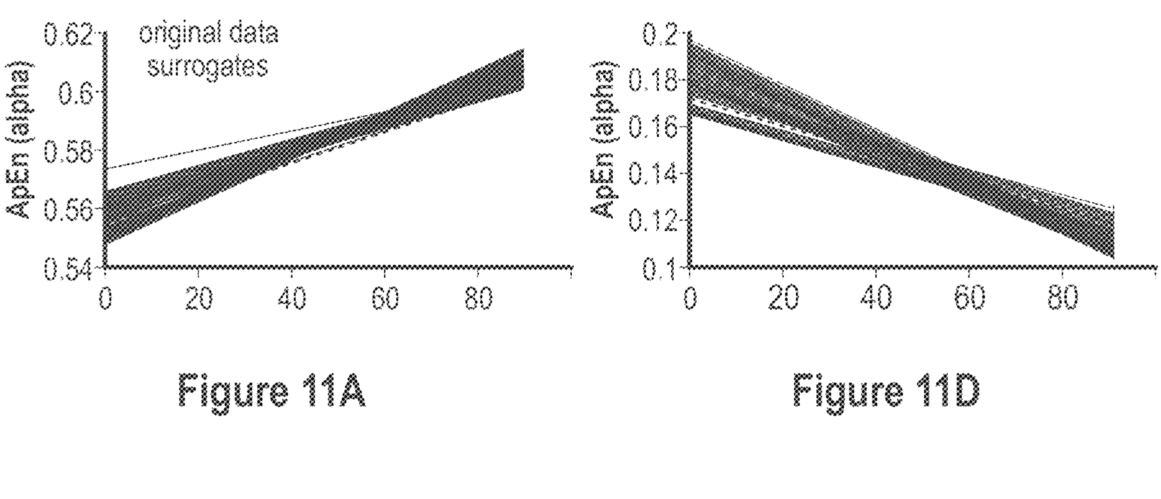
Figure 11A
Figure 11D
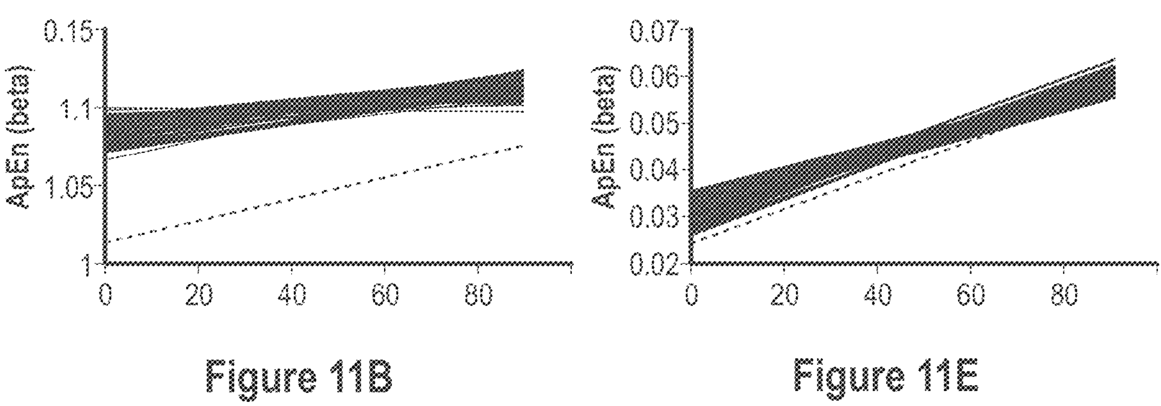
Figure 11B
Figure 11E
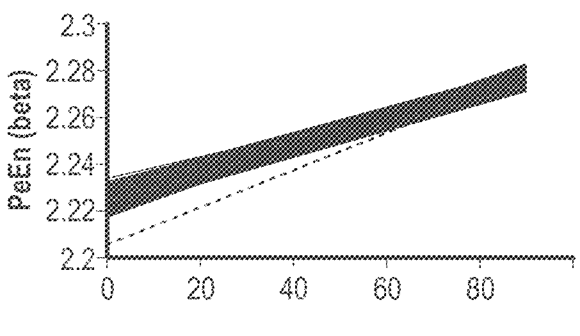
Figure 11C

SYSTEM, METHOD AND COMPUTER-ACCESSIBLE MEDIUM FOR ANESTHESIA MONITORING USING ELECTROENCEPHALOGRAPHIC MONITORING

CROSS-REFERENCE TO RELATED APPLICATION(S)

This application is a continuation of International Patent Application No. PCT/US2020/055414, filed on Oct. 13, 2020 that published as International Patent Publication No. WO 2021/072405 on Apr. 15, 2021, and also relates to and claims priority from U.S. Patent Application Ser. No. 62/914,183, filed on Oct. 11, 2019, and U.S. Patent Application Ser. No. 62/960,947, filed on Jan. 14, 2020, the entire disclosures of which are incorporated herein by reference.

FIELD OF THE DISCLOSURE

The present disclosure relates generally to anesthesia monitoring, and more specifically, to exemplary embodiments of an exemplary system, method, and computer-accessible medium for anesthesia monitoring using electroencephalographic monitoring.

BACKGROUND INFORMATION

There is a strong shift in population demographics towards an aging society. (See, e.g., Reference 1). This shift is going to result in an increased number of surgeries in geriatric patients. (See, e.g., Reference 2). Older patients are at higher risk of developing adverse outcomes like delirious episodes after surgery with general anesthesia. (See, e.g., References 3 and 4). Electroencephalographic ("EEG") monitoring devices may help to estimate the patients' level of neurophysiologic activity and to prevent episodes of excessively high administered doses of anesthesia as characterized by EEG burst suppression. The presence of these episodes seem to represent an independent risk factor for cognitive impairments after anesthesia (See, e.g., References 5 and 6), however some controversy exists regarding strategies designed to reduce the duration of burst suppression. (See, e.g., References 3 and 7).

Despite these possible advantages, the current generation of monitoring devices does not account for age-related changes in EEG characteristics. In general, EEG characteristics during general anesthesia vary greatly among patients of different age and cognitive performance. (See, e.g., References 8-10). Older patients exhibit lower EEG amplitudes (and consequently, lower power) during wakefulness (See, e.g., Reference 11), sleep (See, e.g., Reference 12), and general anesthesia. (See, e.g., References 8 and 9). Previous publications have described age-related changes in power spectral density ("PSD") under general anesthesia to some degree (See, e.g., References 8 and 9), but a detailed description of age-related differences in other aspects of quantitative EEG is still missing. Age-related changes in the EEG recorded from patients from 18 to 90 years under general anesthesia have been investigated with the goal to (i) characterize the EEG of older patients in more detail to further understand the neurophysiological changes that occur with advanced age and to (ii) estimate the influence of these changes on current EEG-based monitoring systems. PSD, normalized PSD ("nPSD"), the 1/f characteristics of the power spectrum, as well as the entropic measures permutation entropy ("PeEn") (See, e.g., Reference 13) and approximate entropy ("ApEn") (See, e.g., Reference 14) were analyzed to investigate age-related changes in the EEG activity. The 1/f characteristic and information extracted from PSD and n(PSD) analysis help to get a good (e.g., more broadband) overview of age-related changes. The entropic measures can help to identify subtler changes in the EEG. These analytical parameters were originally developed to characterize the complexity of a time-series signal and are reported as good measures to estimate the anesthetic level of a patient. (See, e.g., References 15-17). In one example, two parameters beta-ratio (See, e.g., Reference 18) and spectral entropy (See, e.g., Reference 1), were used that are incorporated in current monitoring systems to estimate possible impact of age on the index these systems generate to reflect the (e.g., hypnotic) level of anesthesia.

Thus, it may be beneficial to provide an exemplary system, method, and computer-accessible medium for anesthesia monitoring using electroencephalographic monitoring which can overcome at least some of the deficiencies described herein above.

SUMMARY OF EXEMPLARY EMBODIMENTS

An exemplary system, method, and computer-accessible medium for determining an effect of an age of a patient(s) during an administration of a compound can include, for example, receiving electroencephalographic (EEG) information for the patient(s) during the administration of the compound to the patient(s); and determining the effect of the age of the patient(s) based on the EEG information. A bispectral index of the at least one patient during the administration of the compound, or an entropy of the at least one patient during the administration of the compound can be received, and the effect of the age of the patient(s) can be determined based on the bispectral index, or the entropy. The compound can include an anesthesia. The anesthesia can include (i) sevoflurane, (ii) isoflurane, (iii) dexmedetomidine, (iv) propofol, (v) etomidate, (vi) desflurane, or (vii) a combination of ketamine and nitrous oxide.

In some exemplary embodiments of the present disclosure, a power spectral density (PSD) can be determined based on the EEG information, and the effect of the age of the patient(s) can be determined based on the PSD. A normalized PSD ("nPSD") can be determined based on the PSD, and the effect of the age of the patient(s) can be determined based on the normalized PSD. The nPSD can be determined by, e.g., dividing the PSD by a sum in a particular frequency range, where the particular frequency range can be from about 0.4 Hz to about 30.5 Hz. A spectral entropy of the nPSD can be determined.

A power in a range of about 0.530 Hz can be determined based on PSD, an alpha-band power can be determined based on PSD, a beta-band power can be determined based on PSD, a delta-band power can be determined based on PSD, or theta-band power can be determined based on PSD. The alpha-band power can be, e.g., about 7.8-12.5 Hz, the beta-band power can be about 12.5-25 Hz, the delta-band power can be about 0.4-3.9 Hz, and the theta-band power can be about 3.9-7.8 Hz. The normalized alpha-band power can be determined by dividing a first sum of the PSD in a first range of about 8 Hz to about 12 Hz by a second sum of the PSD in a second range of about 0.4 Hz to about 30 Hz, and the normalized beta-band power can be determined by dividing a third sum of the PSD in a third range of about 12 Hz to about 25 Hz by a fourth sum of the PSD in the second range. The PSD can be decomposed, for example, into a periodic component and an aperiodic component in the EEG information. The aperiodic component can be fit based on a broadband offset, a frequency vector, and a slope.

The EEG information can include EEG information from a frontal region of a brain of the patient(s). An adaptive filtering procedure can be applied to the EEG information, and edge effects cause by the adaptive filtering procedure can be excluded.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIGS. 11A-11E are exemplary graphs illustrating the effect of phase randomization on relative alpha-power and beta-power according to an exemplary embodiment of the present disclosure;

Figure 1:
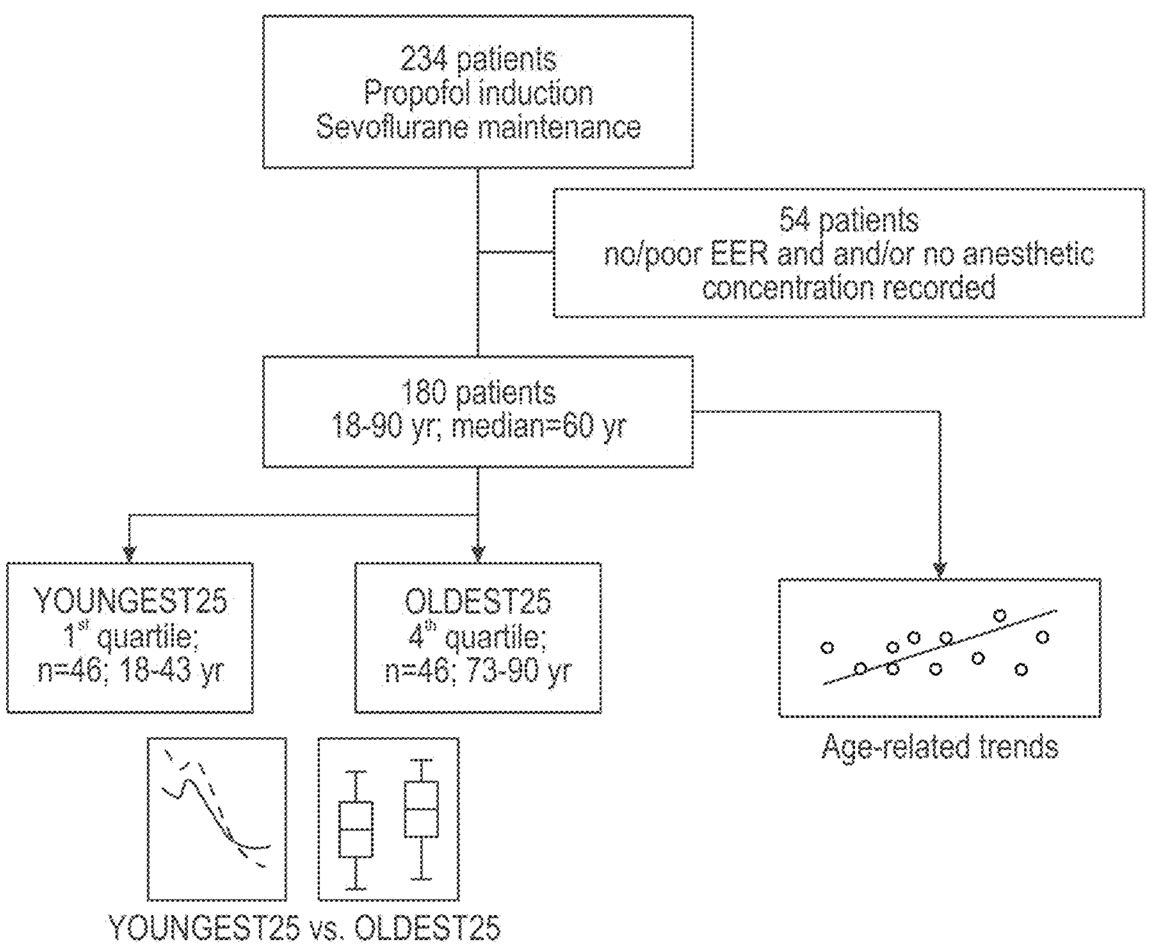
FIG. 1 is an exemplary flow diagram of an exemplary method for excluding patients to define groups for analysis according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

Exemplary embodiments of the present disclosure are described herein using sevoflurane. However, the exemplary system, method and computer-accessible medium, according to an exemplary embodiment of the present disclosure can be used with any suitable anesthesia, as well as other compounds and/or medications. For example, the exemplary system, method and computer-accessible medium can be used with, but is not limited to, isoflurane, dexmedetomidine, propofol, etomidate, desflurane, as well as commonly used doses of ketamine and nitrous oxide.

Frontal EEG records from 180 patients during general anesthesia have been used, which were collected at the Waikato District Health Board Hospital in Hamilton, New Zealand. These patients gave written informed consent, and had contributed to an earlier observational study. (See, e.g., Reference 20). The ethical approval was specifically for the establishment of an anonymous EEG database that could be used for various post-hoc analyses. Patients were selected who had received propofol for induction, and sevoflurane for maintenance of anesthesia. For each patient, ten seconds of artifact-free, non-burst-suppression EEG, recorded five to two minutes were selected prior to the onset of surgery, which represent a clinical level of general anesthesia without any surgical stimulation. EEG with either the bispectral index ("BIS") (e.g., Medtronic, Dublin, Ireland) or the Entropy Module (e.g., GE Healthcare, Helsinki, Finland) monitors was recorded at 128 and 100 Hz respectively. Raw EEG from the BIS was then resampled to 100 Hz for ease of comparison.

Effect-site concentrations of sevoflurane, opioid, and propofol were estimated using standard pharmacokinetic models. The effect-site sevoflurane concentration (e.g., in MAC, CeMAC) was calculated using an end-tidal to brain delay model with a diffusion half-time constant (e.g., Keo) of 144 seconds. (See, e.g., Reference 21). Based on these values, age-adjusted MAC values (e.g., referenced to 1 MAC in a 40 year old, i.e. MAC40) as described by Mapleson were calculated. (See, e.g., Reference 22). Opioid concentration (e.g., in fentanyl-equivalents; 1 ng/ml of fentanyl equals 20 ng/ml of morphine) was calculated using the two-compartment model parameters (See, e.g., Reference 23) for morphine, and for fentanyl. (See, e.g., Reference 24). Effect-site propofol concentrations was estimated according to an exemplary model and exemplary parameters. (See, e.g., Reference 25).

Exemplary EEG Analysis

Exemplary Spectral Analysis

The power spectral density ("PSD") was calculated using Thompson's multitaper power spectral density estimate MATLAB R2015a (e.g., The MathWorks Inc., Natick, MA) pmtm function (e.g., default settings and NFFT=256) was utilized. Based on PSD, the power in the 0.530 Hz range (plus or minus about 10%), the alpha-band power (e.g., about 7.8-12.5 Hz, plus or minus about 10%), and the beta-band power (e.g., about 12.5-25 Hz, plus or minus up to about 10%) as well as the lower frequency delta-band (e.g., about 0.4-3.9 Hz, plus or minus up to about 10%) and theta-band (e.g., about 3.9-7.8 Hz, plus or minus up to about 10%) were calculated. Further, a nPSD was computed by dividing the PSD by the sum from about 0.4 to about 30.5 Hz (plus or minus up to about 10%). The Python was used based FOOOF-toolbox using the provided MATLAB-wrapper (See, e.g., Reference 26) to identify periodic activity as well as the aperiodic component of the EEG. The FOOOF procedure (e.g., fitting oscillations & one over f) decomposes the PSD into periodic components as well as an aperiodic component that reflects 1/f like characteristics. The aperiodic component can be fitted according to L=b-log($F^a$) with b being the broadband offset, F being the frequency vector, and a being the slope. A "knee" parameter was not considered and hence used the "fixed model" as described in the original publication. (See, e.g., Reference 26). The exemplary range was defined to detect possible oscillatory components from 1 to 30 Hz and focused on the detection of these peaks in the alpha range. Furthermore, the relative alpha-band power was obtained by dividing the sum of the PSD in a range of about 8-12 Hz (plus or minus up to about 10%) by a sum of the PSD in a range of about 0.4-30 Hz (plus or minus up to about 10%) and the beta-band power relative power was obtained by dividing the sum of the PSD in the range of about 12-25 Hz (plus or minus up to about 10%) by the sum of PSD in the 0.4-30 Hz range (plus or minus about 10%).

Exemplary Entropy Analysis

Entropic measures can include a time-domain approach to evaluate EEG features. ApEn and PeEn for the EEG 0.5-30 Hz range, the EEG alpha-band, and the EEG beta-band were individually calculated. An adaptive filtering routine (e.g., Butterworth filter, order 3-5) was applied using the MATLAB filtfilt functions that preserves the phase of the signal. So as not to include edge effects caused by filtering, the filter was applied to a 30 s EEG segment and used the central 10 s to calculate the entropies for the different frequency ranges.

For ApEn, and exemplary routine, for PeEn, was utilized, and the my_permutation_entropy function was implemented from MATLAB Central. An embedding dimension m=3 and a time delay 'r=1 for PeEn (See, e.g., Reference 15) and m=2/'r=1 together with tolerance r=0.2 SD for ApEn were selected. (See, e.g., Reference 27). These parameter settings can be commonly used for EEG analyses. (See, e.g., References 14, 16, 27, and 28). ApEn can be used by the exemplary system, method, and computer-accessible medium to determine similar amplitude patterns (e.g., of length m) in the EEG and calculate the probability of the patterns remaining similar if it can be extended to a length of m+1. Similar in this context can include that the amplitude values between the patterns do not differ by more than the defined tolerance r. PeEn as an ordinal measure can code small segments of length m according to their ranks, with the highest amplitude in the segment having the highest rank. PeEn can present the Shannon entropy (See, e.g., Reference 29) of the probability distribution of the possible patterns (e.g., 6, if m=3). A graphical explanation for ApEn and PeEn can be found here. (See, e.g., Reference 30).

Exemplary Phase-Randomized Surrogate Analysis

To delineate the specific contribution of extracting information from the entropic measures versus the spectral measures of a signal, phase-randomized surrogate data was utilized. For example, 200 phase-randomized surrogates have been calculated for each of the 180 EEG episodes and compared the entropic measures to the spectral EEG band powers. For surrogate generation, a modified version of the surrogate function was utilized for phase randomization of the PhysioNet Toolkit. (See, e.g., Reference 31). This function was modified so that no amplitude transformation, and only a phase randomization was performed. Then, the ApEn and PeEn were calculated for the alpha and beta range as well as the relative alpha-ad beta band power for the surrogates.

Exemplary Parameters for Comparison to Available Monitors

In order to estimate the influence of age on available monitoring systems like the BIS and Entropy module, the beta ratio=log(sum(PSD30-47 Hz)/sum(PSD11-20 Hz)) was calculated as proxy for the sub-parameter BetaRatio of the BIS. (See, e.g., Reference 32). Further, the spectral entropy ("SpEnt") of the nPSD was calculated for settings mimicking the state entropy ("SE") (e.g., to 32 HZ) and response entropy ("RE") (e.g., 47 Hz) for different lower band limits of 0.8 and 1.1 Hz. (See, e.g., Reference 19). For 168 of the 180 patients, for example, BIS indices were available. In order to evaluate the influence of age on BIS, the last index value displayed within the 10 s analysis window was used, for example, for spectral and entropic analysis.

Exemplary Statistical Analysis

Because of the retrospective nature of the investigation according to the exemplary embodiments of the present disclosure, statistical power calculation was not conducted prior to the review and the sample size was based on the available number of patient EEG. The exemplary spectral analyses (e.g., except the spectral entropy with the 1.1 Hz lower limit) were a priori and the entropic analyses (e.g., approximate entropy, permutation entropy) according to exemplary embodiments of the present disclosure, were post hoc analyses after evaluating different parameter settings.

Exemplary Regression Analyses

Exemplary models were generated by the embodiments of the exemplary system, method, and computer-accessible medium using, for example, the least squares method for linear regression analysis for each dependent variable with respect to age. For each linear model, the regression curve was generated and a one-sample t-test comparing the slope coefficient against a slope of zero was performed. Additionally, the exemplary strength of the correlation was determined (e.g., the fit of the model as an $R^2$ value).

Exemplary Evaluation of Interaction Between Sevoflurane Concentration and EEG Parameter In order to evaluate if the EEG parameter (e.g., PeEn and ApEn) differs significantly based on an interaction between age and age-adjusted MAC at a 5% significance level, the exemplary linear model interaction terms were calculated using the MATLAB fitlm function.

Exemplary Comparison of the Youngest Versus the Oldest Quartiles

For each parameter, the youngest 25% (e.g., n=46, $1^{st}$ quartile, Y25) and the oldest 25% (e.g., n=46, $4^{th}$ quartile, O25) of patients were compared using a Mann-Whitney U test at a confidence level of 95% together with the area under the receiver operator characteristics curve ("AUC") and 10000-fold bootstrapped 95% confidence intervals ("CI") as effect size. The MATLAB-based MES toolbox was used for AUC and 95% CI calculation. (See, e.g., Reference 33). By including all subjects of a certain age youngest and oldest quartiles each contained 46 subjects (e.g., not 45). The exemplary model excluded middle age range (e.g., 44 to—72 years old) contained 88 instead of the expected 90 subjects. According to the traditional academic point system, AUC values can be interpreted as excellent: 1≥AUC≥0.9; good: 0.9>AUC≥0.8; fair: 0.8>AUC≥0.7; poor: 0.7>AUC≥0.6; or fail: AUC<0.6. For the (n) PSD comparison, significant results were defined if at least two neighboring frequencies showed significant differences between the young and old group. This procedure has been applied for similar studies, by other groups. (See, e.g., Reference 34). For example, all tests applied were two-tailed tests and $p<0.05$ was considered being significant.

Exemplary Results

Of the 234 patients undergoing surgical intervention with propofol induction and sevoflurane maintenance, 54 patients were excluded from analysis due to missing EEG or incomplete volatile anesthetic concentrations data in the period prior to surgery onset, resulting in 180 patients being included in the final analysis. The subject ages ranged from 18 to 90 y (e.g., mean ("SD")=56.7 (18.4) y). The age range for Y25 was from 18 to 43 years and for O25 from 73 to 90 years. FIG. 1 shows an exemplary flow chart of patient and group selection. The exemplary results of all linear regressions as well as all the comparisons between Y25 and O25 are presented in Table 1 below.

TABLE 1

| Parameter | intercept | slope | 95% CI slope | t-Stat | p slope | R2 |
|---|---|---|---|---|---|---|
| absolute delta pwr | 37.66 | −0.15 | [−0.18 −0.13] | −10.99 | <0.001 | 0.40 |
| absolute theta pwr | 29.82 | −0.17 | [−0.20 −0.15] | −13.13 | <0.001 | 0.49 |
| absolute alpha pwr | 30.71 | −0.18 | [−0.20 −0.15] | −12.25 | <0.001 | 0.46 |
| absolute beta pwr | 23.02 | −0.13 | [−0.16 −0.10] | −9.74 | <0.001 | 0.35 |
| relative delta pwr | 0.69 | 0.000 | [−0.001 0.002] | 0.53 | 0.599 | 0.00 |
| relative theta pwr | 0.11 | 0.000 | [−0.001 0.000] | −0.77 | 0.445 | 0.00 |
| relative alpha pwr | 0.17 | −0.001 | [−0.002 0.000] | −1.36 | 0.176 | 0.01 |
| relative beta pwr | 0.02 | 0.000 | [−0.000 0.001] | 1.78 | 0.077 | 0.02 |
| exp of FOOOF | 2.65 | −0.009 | [−0.011 −0.007] | −8.14 | <0.001 | 0.27 |
| offset of FOOOF | -0.43 | −0.008 | [−0.009 −0.006] | −8.27 | <0.001 | 0.29 |
| PeEn 0.5-30 | 1.97 | 0.002 | [0.001 0.003] | 7.04 | <0.001 | 0.22 |
| PeEn delta | 1.34 | 0.000 | [−0.000 0.001] | 1.67 | 0.097 | 0.02 |
| PeEn theta | 1.72 | 0.000 | [−0.000 0.000] | 1.12 | 0.263 | 0.01 |
| PeEn alpha | 1.92 | 0.000 | [−0.000 0.000] | 0.69 | 0.489 | 0.00 |
| PeEn beta | 2.21 | 0.001 | [0.001 0.001] | 4.95 | <0.001 | 0.12 |
| ApEn 0.5-30 | 0.76 | 0.002 | [0.001 0.003] | 4.87 | <0.001 | 0.12 |
| ApEn delta | 0.41 | −0.001 | [−0.001 −0.001] | −2.20 | 0.029 | 0.03 |
| ApEn theta | 0.62 | 0.000 | [−0.000 0.000] | −1.95 | 0.052 | 0.02 |
| ApEn alpha | 0.55 | 0.001 | [0.000 0.001] | 4.18 | <0.001 | 0.09 |
| ApEn beta | 1.01 | 0.001 | [0.001 0.001] | 2.44 | 0.016 | 0.03 |
| BIS | 33.96 | 0.16 | [0.078 0.24] | 3.84 | <0.001 | 0.08 |
| BETA RATIO | −4.74 | 0.02 | [0.01 0.02] | 5.00 | <0.001 | 0.12 |
| SpEnt(1.1-32) | 2.73 | 0.007 | [0.005 0.01] | 5.81 | <0.001 | 0.16 |
| SpEnt(1.1-47) | 2.73 | 0.007 | [0.005 0.010] | 6.08 | <0.001 | 0.17 |
| SpEnt(0.8-32) | 2.64 | 0.002 | [−0.002 0.005] | 0.79 | 0.433 | 0.00 |
| SpEnt(0.8-47) | 2.64 | 0.002 | [−0.002 0.006] | 0.37 | 0.372 | 0.00 |

| Parameter | YOUNG | OLD | p (ranksum) | AUC |
|---|---|---|---|---|
| absolute delta pwr | 32.72 [30.80 35.87] | 5.98 [23.90 28.36] | <0.001 | 0.94 [0.89 0.98] |
| absolute theta pwr | 24.13 [22.33 26.93] | 16.02 [13.85 19.27] | <0.001 | 0.93 [0.86 0.98] |
| absolute alpha pwr | 24.81 [21.85 28.19] | 17.77 [15.31 19.72] | <0.001 | 0.92 [0.86 0.98] |
| absolute beta pwr | 18.30 [16.29 21.04] | 13.75 [10.02 15.24] | <0.001 | 0.90 [0.83 0.96] |
| relative delta pwr | 0.76 [0.69 0.82] | 0.75 [0.63 0.83] | 0.806 | 0.52 [0.40 0.63] |
| relative theta pwr | 0.10 [0.07 0.12] | 0.09 [0.06 0.13] | 0.375 | 0.55 [0.43 0.68] |
| relative alpha pwr | 0.10 [0.08 0.17] | 0.10 [0.07 0.17] | 0.693 | 0.52 [0.42 0.63] |
| relative beta pwr | 0.03 [0.02 0.04] | 0.04 [0.02 0.06] | 0.041 | 0.62 [0.52 0.73] |
| exp of FOOOF | 2.36 [2.19 2.60] | 2.00 [1.89 2.16] | <0.001 | 0.84 [0.76 0.92] |
| offset of FOOOF | −0.59 [−0.90 −0.48] | −0.96 [−1.15 −0.85] | <0.001 | 0.81 [0.71 0.89] |
| PeEn 0.5-30 | 2.02 [1.98 2.07] | 2.11 [2.06 2.15] | <0.001 | ~~0.19 [0.10 0.29]~~ 0.81 [0.71 0.90] |
| PeEn delta | 1.35 [1.32 1.37] | 1.36 [1.34 1.38] | 0.129 | ~~0.41 [0.30 0.52]~~ 0.59 [0.48 0.70] |
| PeEn theta | 1.72 [1.70 1.75] | 1.73 [1.71 1.75] | 0.219 | ~~0.43 [0.29 0.56]~~ 0.57 [0.44 0.71] |
| PeEn alpha | 1.92 [1.91 1.95] | 1.93 [1.91 1.95] | 0.384 | ~~0.45 [0.33 0.57]~~ 0.55 [0.43 0.67] |
| PeEn beta | 2.24 [2.20 2.27] | 2.27 [2.24 2.29] | <0.001 | ~~0.29 [0.20 0.39]~~ 0.71 [0.61 0.80] |
| ApEn 0.5-30 | 0.83 [0.77 0.89] | 0.93 [0.84 0.99] | <0.001 | ~~0.24 [0.15 0.34]~~ 0.76 [0.66 0.85] |
| ApEn delta | 0.40 [0.34 0.44] | 0.37 [0.33 0.41] | 0.088 | 0.60 [0.50 0.70] |
| ApEn theta | 0.61 [0.61 0.62] | 0.61 [0.60 0.62] | 0.143 | 0.59 [0.46 0.71] ~~0.31 [0.22 0.40]~~ |

TABLE 1-continued

| | | | | |
|---|---|---|---|---|
| ApEn alpha | 0.57 [0.56 0.59] | 0.60 [0.57 0.62] | 0.002 | 0.69 [0.60 0.78] |
| ApEn beta | 1.05 [1.00 1.08] | 1.08 [1.03 1.12] | 0.007 | ~~0.34 [0.22 0.45]~~ 0.66 [0.55 0.77] |
| BIS | 42 [32 44] | 45 [40 51] | 0.026 | ~~0.35 [0.24 0.48]~~ 0.65 [0.52 0.76] |
| BETA RATIO | −4.20 [−4.63 −3.71] | −3.61 [−4.02 −3.27] | <0.001 | ~~0.27 [0.18 0.37]~~ 0.73 [0.63 0.82] |
| SpEnt(1.1-32) | 3.02 [2.78 3.17] | 3.25 [3.13 3.46] | <0.001 | ~~0.21 [0.13 0.30]~~ 0.79 [0.70 0.87] |
| SpEnt(1.1-47) | 3.02 [2.79 3.18] | 3.29 [3.18 3.47] | <0.001 | ~~0.20 [0.12 0.29]~~ 0.80 [0.71 0.88] |
| SpEnt(0.8-32) | 2.72 [2.31 2.91] | 2.78 [2.50 3.16] | 0.202 | ~~0.42 [0.32 0.53]~~ 0.58 [0.47 0.68] |
| SpEnt(0.8-47) | 2.73 [2.31 2.91] | 2.79 [2.51 3.16] | 0.161 | ~~0.42 [0.31 0.53]~~ 0.58 [0.47 0.69] |

Exemplary Medications

Despite the lack of any prescribed anesthetic protocol, the delivered sevoflurane concentration was lower in the older patients. It can be possible to reduce or even eliminate this trend by age-adjusting the MAC according to Mapleson. (See, e.g., Reference 22). Similarly, the estimated propofol concentration decreased with age. By contrast, exemplary data did not reveal any age-related difference in the opioid concentrations, measured in fentanyl equivalents. FIGS. 6A-6D show exemplary graphs illustrating drug dose to age relationships according to an exemplary embodiment of the present disclosure. While the relationships for propofol and sevoflurane and age were statistically significant, the $R^2$-values were rather low (e.g., $R^2 \leq 0.06$), indicating substantial contribution by other unmeasured factors. These exemplary results can reflect that the providers in exemplary review consider age in their titration of dosages of propofol and sevoflurane but other nuanced factors go into decisions on opioid administration (e.g., surgery type, hemodynamic changes).

As shown in FIGS. 6A-6D, there was a linear trend between sevoflurane MAC and age, before age adjustment. After age adjustment (See, e.g., Reference 19), there was no significant trend for sevoflurane MAC and age. There was also a trend with residual propofol and age. However, there was no significant trend between opioids delivered and age. Additionally, older patients exhibit a more uniform distribution of relative spectral power. In the regression plots, dots 605 present the single patients and line 610 represents the linear fit. In the boxplots, circles indicate outliers as defined by the MATLAB plotting routine. They were not excluded from analysis.

Figures 7A, 7B:
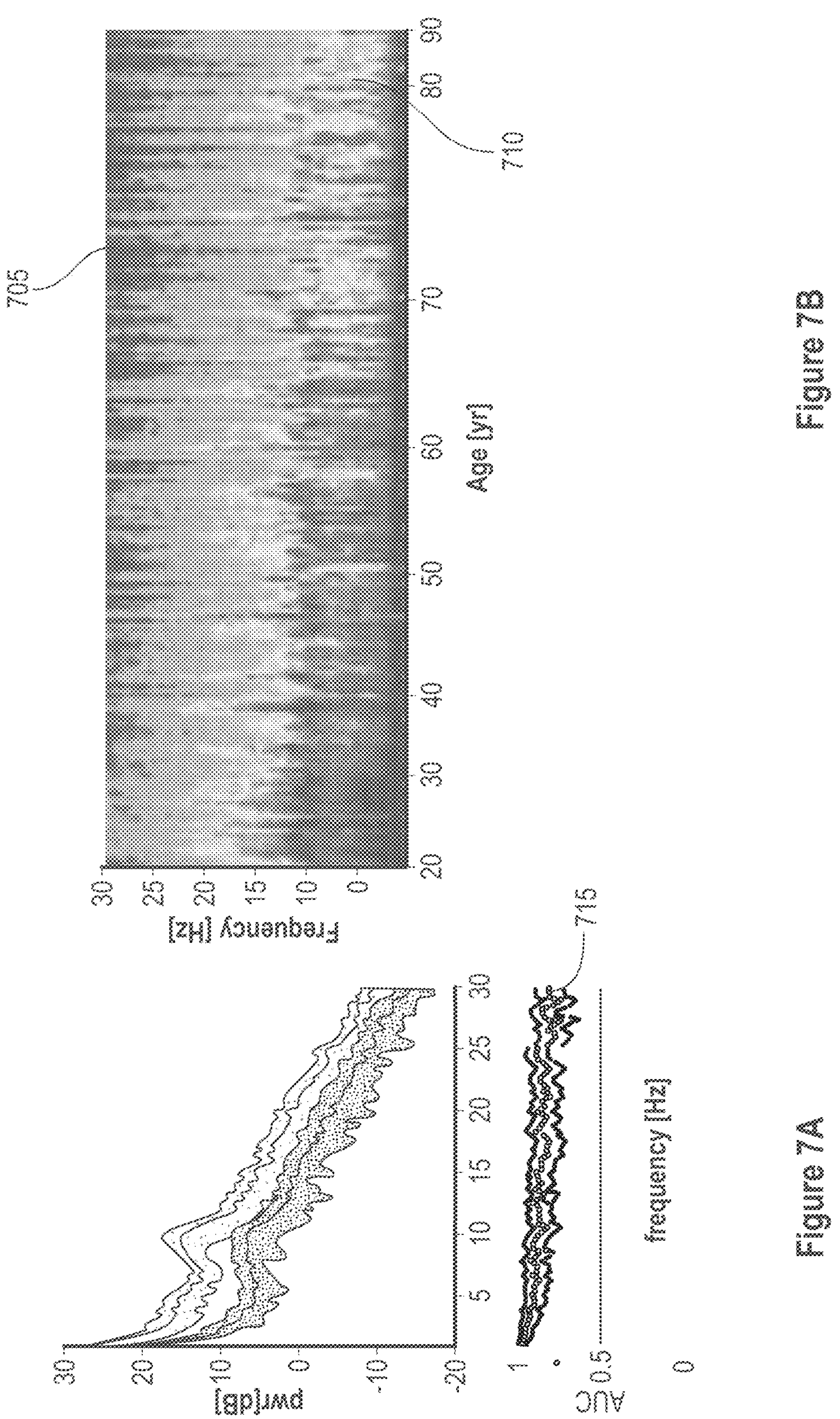
FIG. 7A is an exemplary graph illustrating age versus power relationship according to an exemplary embodiment of the present disclosure.
FIG. 7B is an exemplary graph illustrating age versus frequency according to an exemplary embodiment of the present disclosure.

Very similar age to PSD relationships as presented in a previous study (See, e.g., Reference 9) were obtained, and the exemplary results and the corresponding plots provided as shown in FIGS. 7A and 7B. The nPSD showed significant differences only in the low (e.g., 0.5-5 Hz) and high (e.g., >21 Hz) frequency ranges when comparing Y25 versus O25 patients. For example, FIGS. 2A-2C show exemplary graphs of normalized power spectral density, exemplary row EEG traces, and the aperiodic (e.g., 1/f) component from young and old patients according to an exemplary embodiment of the present disclosure.

Figures 2A, 2B, 2C:
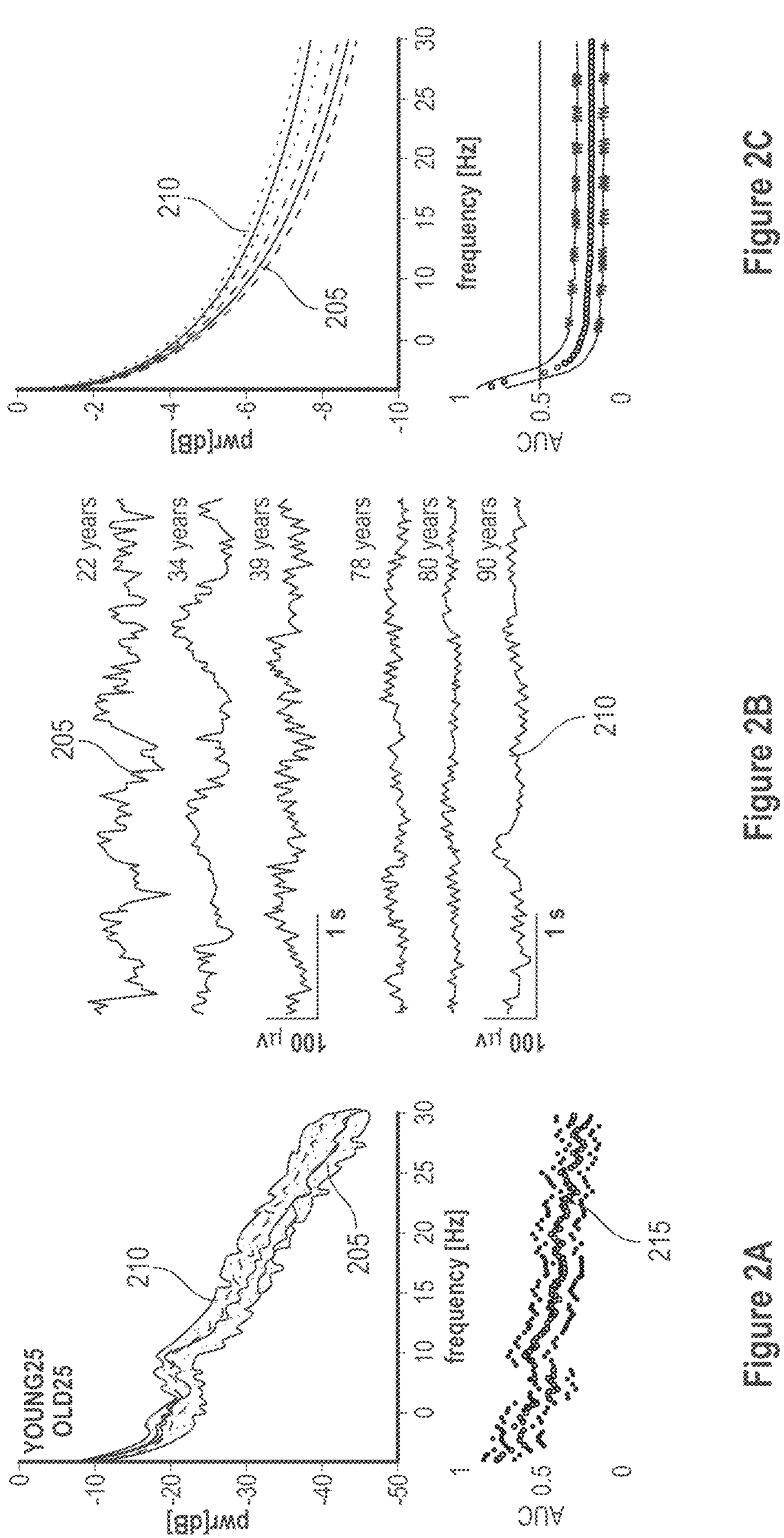
FIGS. 2A-2C are exemplary graphs illustrating normalized power spectral density, exemplary row EEG traces, and the aperiodic (1/f) component from young and old patients according to an exemplary embodiment of the present disclosure.

FIGS. 2A-2C illustrate the median (e.g., ±median absolute deviation) nPSD plots of EEG derived from the 25% youngest (Y25, line/area 205) and 25% oldest (O25, line/area 210) patients of the data set, according to exemplary embodiments of the present disclosure. PSD can be presented with corresponding AUC values and bootstrapped 95% confidence intervals. The relative PSD indicated a more uniform distribution of the EEG from the old group with lower relative power at low frequencies (e.g., 0.5-5 Hz) and higher relative power at high frequencies (e.g., >21 Hz). Exemplary raw EEG traces from patients in the Y25 group (e.g., line/area 205) and O25 group (e.g., line/area 210). These traces highlight the age-induced differences on the EEG, especially fewer slow oscillations and an increased amount of high frequent activity. Median (e.g., ±median absolute deviation) of the exponential fit of the aperiodic (e.g., background) 1/f component between the 25% youngest (e.g., Y25, line/area O25) and 25% oldest (e.g., O25, line/area 210) patients. In addition, the AUC values and 95% bootstrapped confidence intervals are presented. The aperiodic component of the PSD was more uniformly distributed in the old patients. Filled circles 215 indicate a significant difference, between Y25 and O25 evaluated by AUC confidence intervals excluding 0.5.

FIGS. 7A and 7B show median (e.g., ±median absolute deviation) absolute PSD plots of EEG derived from the 46 youngest (e.g., area 705) and 46 oldest (e.g., area 710) patients of the data set, according to exemplary embodiments of the present disclosure. PSD can be presented with corresponding AUC values and bootstrapped 95% confidence intervals. Solid dots 715 indicate a significant difference between old and young. Absolute PSD for each single patient was sorted by age displayed as heat map or spectral array. With age the colors tend to become colder in all frequencies, reflecting the age-dependent decrease in spectral power.

Figures 8A, 8B, 8C, 8D:
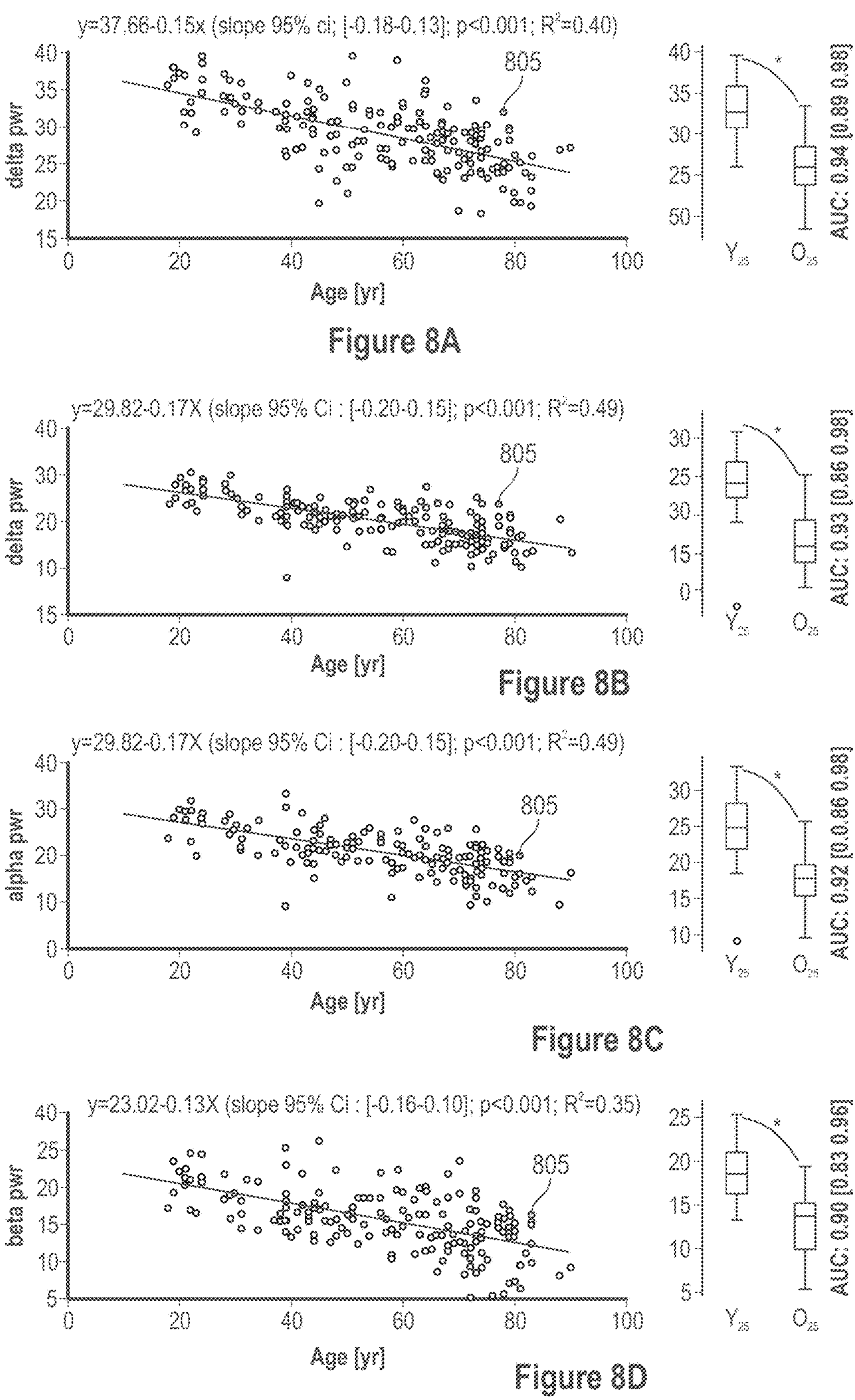
FIGS. 8A-8D are exemplary regression plots and box plots for which measure power versus age according to an exemplary embodiment of the present disclosure.

FIGS. 8A-8D show exemplary regression plots and box plots, according to exemplary embodiments of the present disclosure, for which measure power versus age and corresponding youngest (e.g., Y25) vs. oldest (e.g., O25) quartile box plot for the delta power (see, e.g., FIG. 8A), the theta power (see, e.g., FIG. 8B), absolute EEG alpha power (see, e.g., FIG. 8C) and the absolute EEG beta power (see, e.g., FIG. 8D). Delta power decreased with age (e.g., $p<0.001$, t-statistic−10.99) and age had an excellent and significant (e.g., $p<0.001$, (e.g., AUC=0.94 [0.89 0.98])) effect as depicted in the Y25 vs. O25 boxplot. Theta power decreased with age (e.g., $p<0.001$, t-statistic−13.13) and age had an excellent and significant (e.g., $p<0.001$, (e.g., AUC=0.93 [0.86 0.98])) effect as depicted in the Y25 vs. O25 boxplot. Power in the alpha-band EEG significantly (e.g., $p<0.001$, t-statistic−12.25) decreased with age. Age had had an excellent and significant (e.g., $p<0.001$, AUC=0.92 [0.86 0.98]) effect on absolute alpha-band power as depicted in the Y25 vs. O25 boxplot. EEG beta power significantly (e.g., $p<0.001$, t-statistic−9.74) decreased with age, and had an excellent and significant (e.g., AUC=0.90 [0.83 0.96]) and significant (e.g., p<0.001) effect as depicted in the Y25 vs. O25 boxplot. In the regression plots, dots 805 present the single patients and the blue line the linear fit.

Figure 3A:
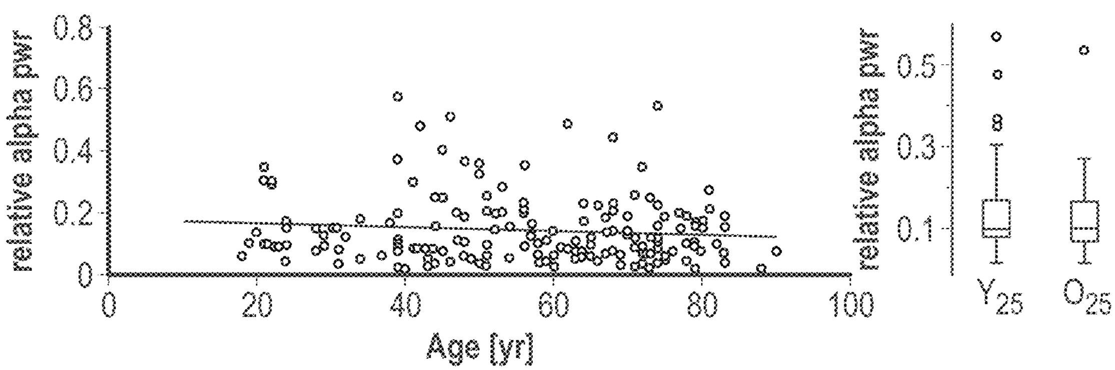
FIGS. 3A-3C are exemplary regression and box plots illustrating relative EEG alpha power, relative EEG Beta power, and the slope of the aperiodic 1/f component according to an exemplary embodiment of the present disclosure.
Figure 3B:
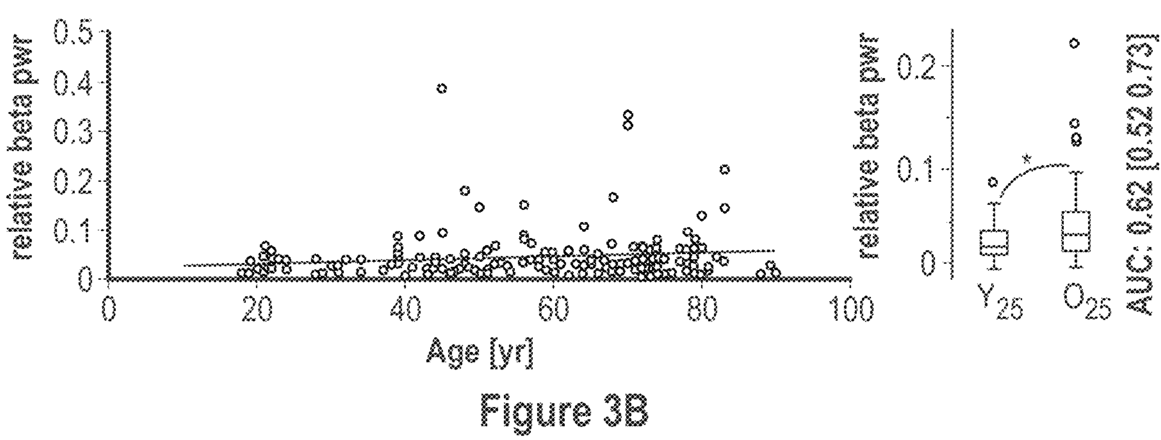
Figure 3C:
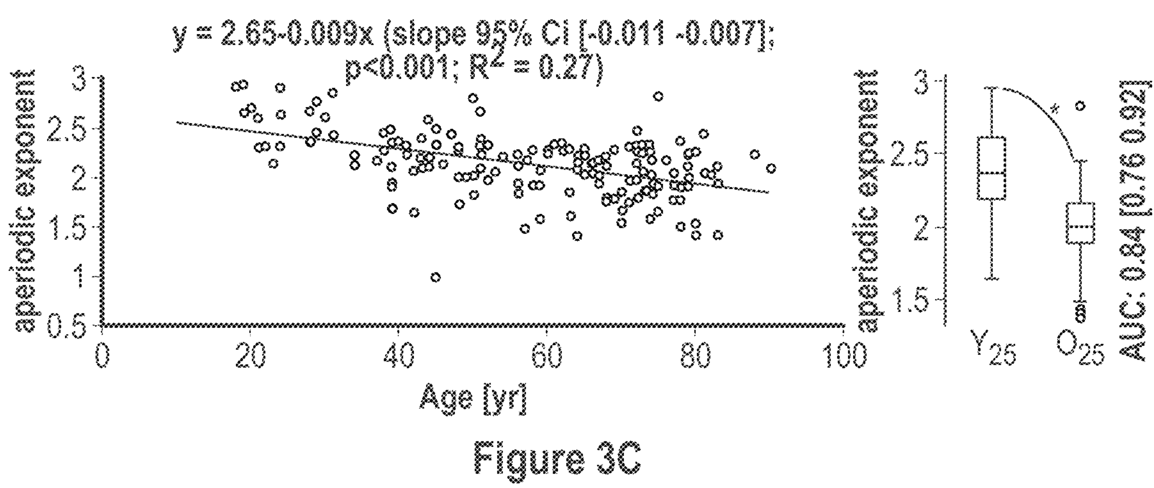

FIGS. 3A-3C show exemplary regression and box plots illustrating relative EEG alpha power, relative EEG Beta power, and the slope of the aperiodic 1/f component, according to an exemplary embodiment of the present disclosure. Significant differences between Y25 and O25 in nPSD in the EEG alpha range (e.g., p=0.693; AUC=0.52 [0.42 0.63]) were not located, but a "poor" and significant effect (e.g., p=0.041; AUC=0.62 [0.52 0.73]) in the EEG beta range as a linear relationship of age with relative alpha and beta power and the difference in relative beta power were not observed.

Exemplary linear regression and box plots are shown for the youngest (e.g., Y25) vs. the oldest (e.g., O25) quartile for the relative EEG alpha power (see e.g., FIG. 3A), the relative EEG beta power (see e.g., FIG. 3B), and the slope of the aperiodic 1/f component with corresponding box plots (see e.g., FIG. 3C). Relative power in the alpha-band EEG did not significantly (e.g., p=0.176, t-statistic: −1.36) change with age. There was no significant difference (e.g., p=0.693, AUC=0.52 [0.42 0.63]) in relative alpha power between Y25 (e.g., 0.10 [0.08 0.17]) and O25 (e.g., 0.10 [0.07 0.17]). Relative EEG beta power did not significantly (e.g., p=0.077, t-statistic: 1.78) change with age, but there was a significant difference (e.g., p=0.041) in relative beta power between Y25 (e.g., 0.03 [0.02 0.04]) and O25 (e.g., 0.04 [0.02 0.06]). The AUC=0.62 [0.52 0.73] 0.38 as effect site indicated a "poor" effect. The slope of the aperiodic 1/f component derived by the FOOOF procedure significantly decreased with age (e.g., p<0.001, t-statistic: −8.14). The box plot indicates a significant flatter (e.g., p<0.001) slope in the O25 patients (e.g., median [1st 3$^{rd}$ quartile]: 2.00 [1.89 2.16]) compared to the Y25 (e.g., 2.36 [2.19 2.604]). The AUC=0.84 [0.76 0.92] as effect site indicated a "good" effect.

These exemplary results provide evidence that age induces a change in the EEG, but that these changes may not be reliably detected by using the power in the classical frequency ranges. The evaluation of the relative power in the lower frequency delta and theta band did not show any age induced effects as well. (See, e.g., FIGS. 9A and 9B).

Figures 9A, 9B:
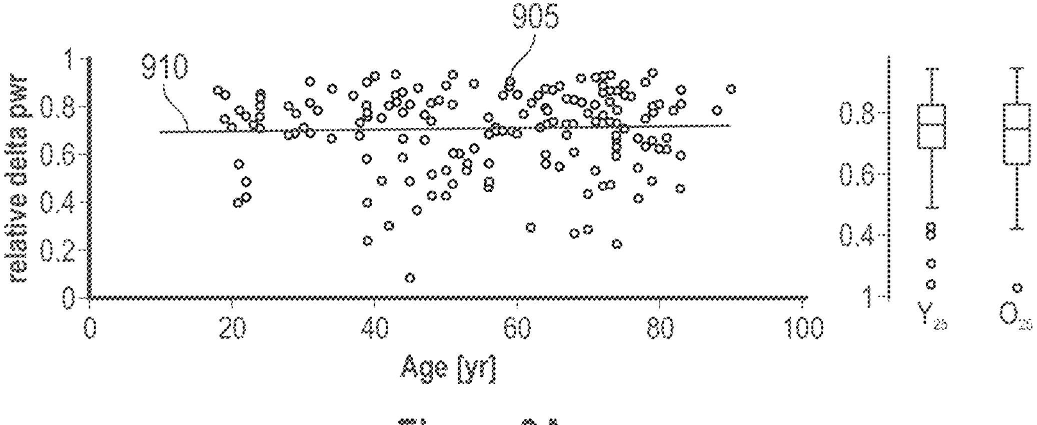
FIG. 9A is an exemplary regression plot and box plot illustrating relative delta power versus age according to an exemplary embodiment of the present disclosure.
FIG. 9B is an exemplary regression plot and box plot illustrating relative theta power versus age according to an exemplary embodiment of the present disclosure.
Figures 10A, 10B, 10C, 10D:
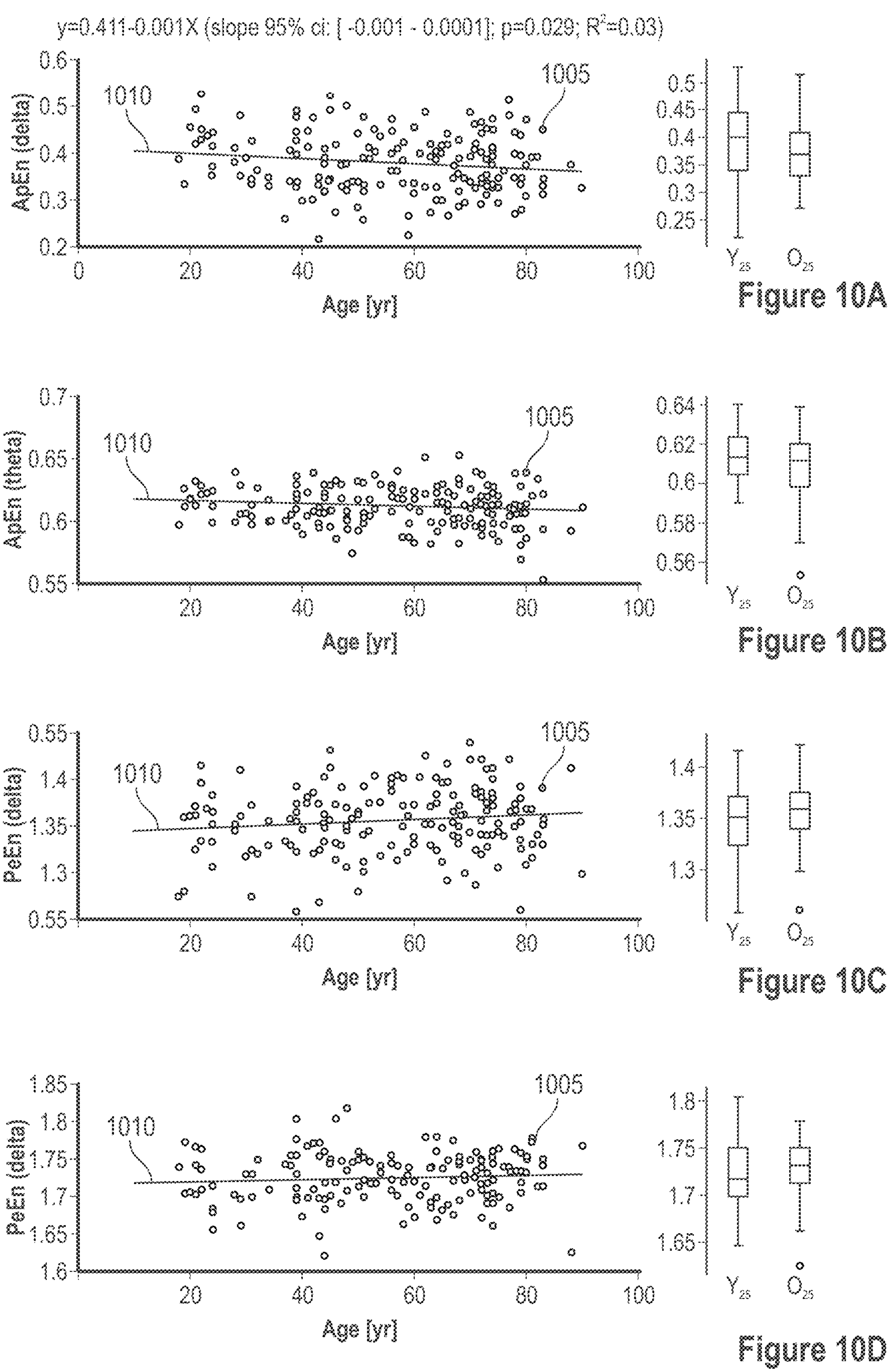
FIGS. 10A-10D are exemplary graphs illustrating regression and box plots based on the exemplary data provided in Table 1 according to an exemplary embodiment of the present disclosure.

For example, FIGS. 9A and 9B show linear regression and box plots of the youngest (e.g., Y25) vs. the oldest (e.g., O25) quartile for relative EEG delta power (see, e.g., FIG. 9A) and the relative EEG theta power (see, e.g., FIG. 9B), according to exemplary embodiments of the present disclosure. Neither of such exemplary plots showed an age-related trend. In the regression plots, dots 905 represent the single patients and line 910 represents the linear fit.

The FOOOF analysis revealed that in 174/180 patients (e.g., 97%) at least one oscillatory component in the 8-12 Hz alpha range could be observed. Because the six patients without such a periodic component were distributed over the age range, these patients can be included. The parameters of the aperiodic component of the nPSD changed with age. (See e.g., FIG. 3C). For the comparison between Y25 and O25 the exponent was affected significantly and strongly (e.g., p<0.001, AUC=0.84 [0.76 0.92]) by age as was the offset (e.g., p<0.001, AUC=0.81 [0.71 0.89]. FIG. 2C shows the more uniform distribution of the aperiodic 1/f component of the PSD in the old patients.

Age Related Changes can be Observed Using Entropy-Based Analyses

Figure 4A:
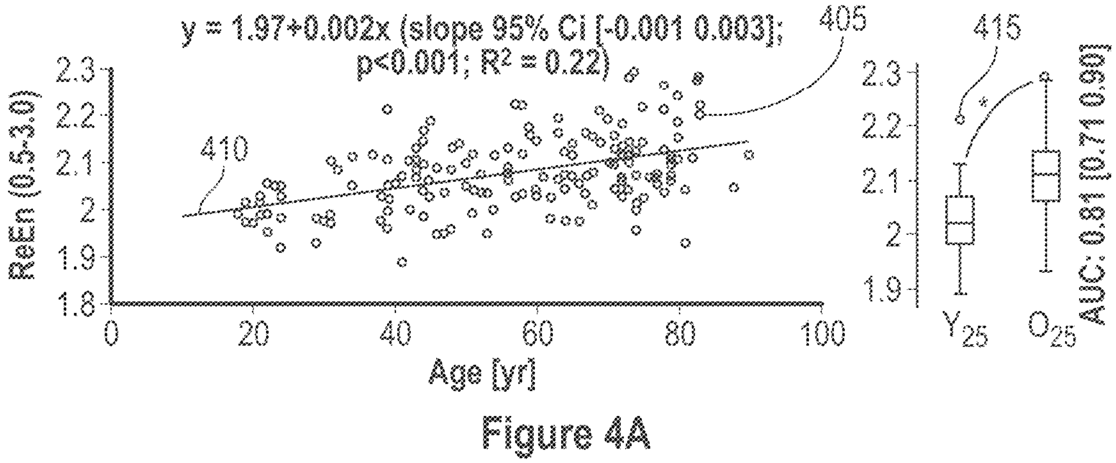
FIGS. 4A-4C are exemplary regression and box plots illustrating the 0.5-30 Hz EEG range, the EEG alpha range, and the EEG beta range according to an exemplary embodiment of the present disclosure.
Figure 4B:
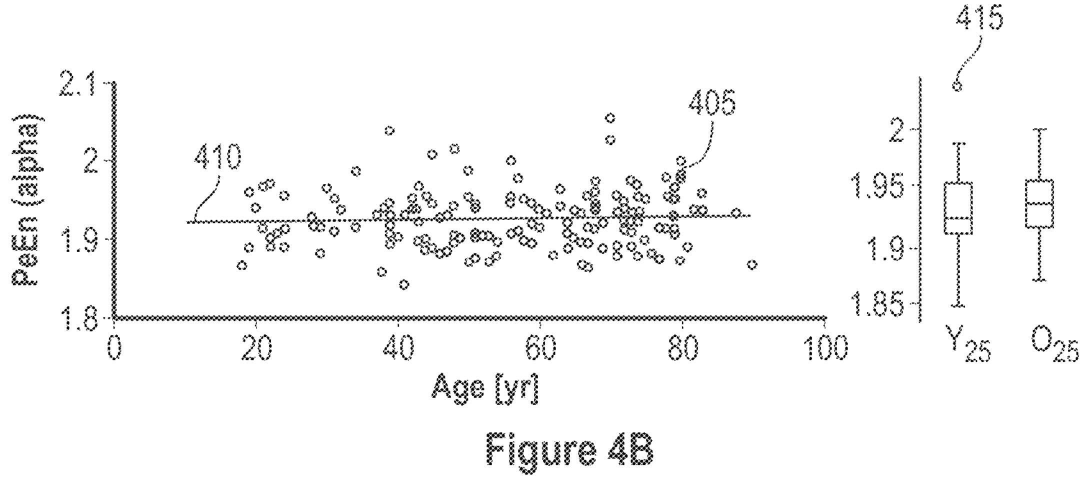

PeEn increased with age in the 0.5-30 Hz range as well as in the EEG beta range, but not in the EEG alpha range. (See, e.g., FIGS. 4A-4C). Comparing Y25 and O25, it was determined strong and significant (e.g., p<0.001, AUC=0.81 [0.71 0.90]) effect of age on the (e.g., 0.5-30 Hz) filtered EEG and a fair and significant (e.g., p=0.0006, AUC=0.71 [0.61 0.81]) effect on the beta-band EEG. No significant difference for the alpha-band EEG (e.g., AUC=0.55 [0.43 0.67], p=0.384) was located. These exemplary results signify that PeEn tracks the shift towards higher-frequency EEG activity with age.

Figure 4C:
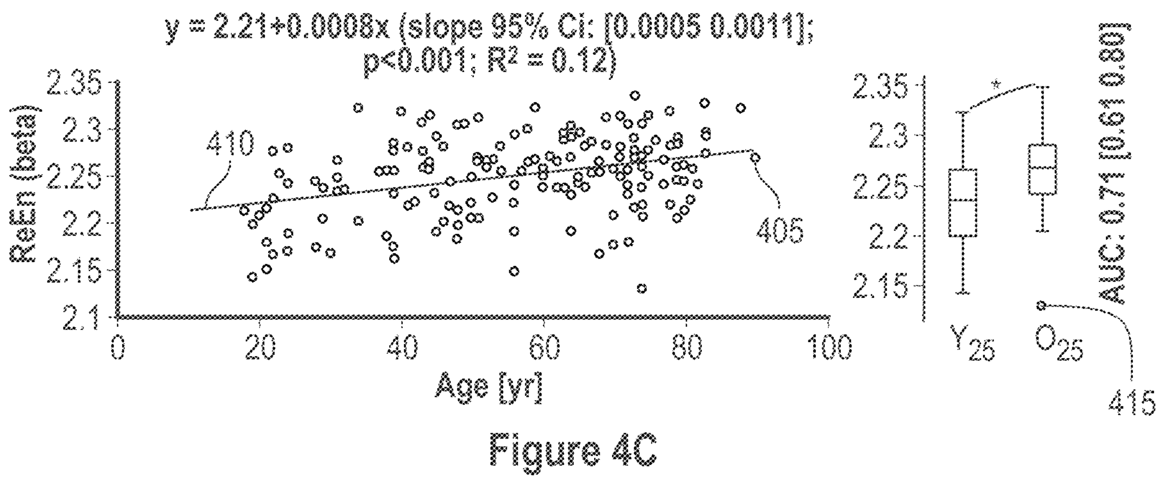

The PeEn (e.g., m=3, τ=1) is shown for the linear regression and box plots of the youngest (e.g., Y25) vs. the oldest (e.g., O25) quartile for 0.5-30 Hz EEG range (See e.g., FIG. 4A), the EEG alpha range (See e.g., FIG. 4B), and the EEG beta range (See e.g., FIG. 4C). PeEn of the 0.5-30 Hz filtered EEG significantly increased (e.g., p<0.001, t-statistic: 7.04) with age. Age had a "good" and significant (e.g., p<0.001; AUC=0.81 [0.71 0.90] 0.19 10.10 0.291) effect on PeEn as depicted in the comparison between Y25 (e.g., 2.02 [1.98 2.07]) and O25 (e.g., 2.11 [2.06 2.15]). PeEn of the alpha-band EEG showed no significant age-related effect (e.g., p=0.489, t-statistic: 0.69) and the AUC for the comparison between Y25 and 025 indicated no effect (e.g., p=0.384; AUC=0.55 [0.43 0.67]). PeEn of the beta-band EEG significantly (e.g., p>0.001, t-statistic: 4.95) increased with age. Age had a "fair" and significant (e.g., p<0.001; AUC=0.71 [0.61 0.80] 0.29 10.20 0.391) effect on PeEn as depicted in the comparison between Y25 (e.g., 2.24 [2.20 2.27]) and O25 (e.g., 2.27 [2.24 2.29]). In the regression plots, dots 405 present the single patients and lines 410 represent the linear fit. In the boxplots, circles 415 indicate outliers as defined by the MATLAB plotting routine.

Figure 5A:
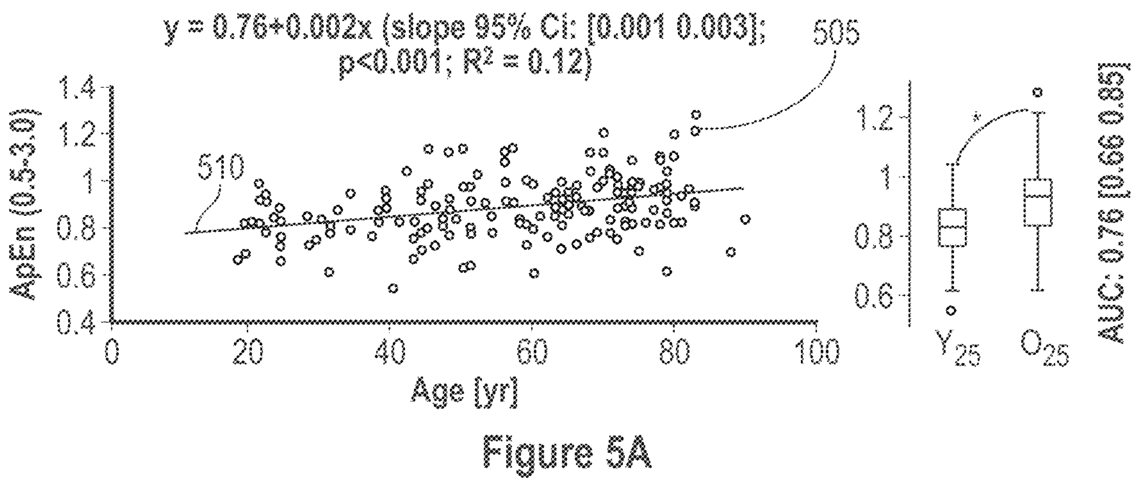
FIGS. 5A-5C are exemplary regression and box plots illustrating the 0.5-30 Hz EEG range, the EEG alpha range, and the EEG beta range according to an exemplary embodiment of the present disclosure.
Figure 5B:
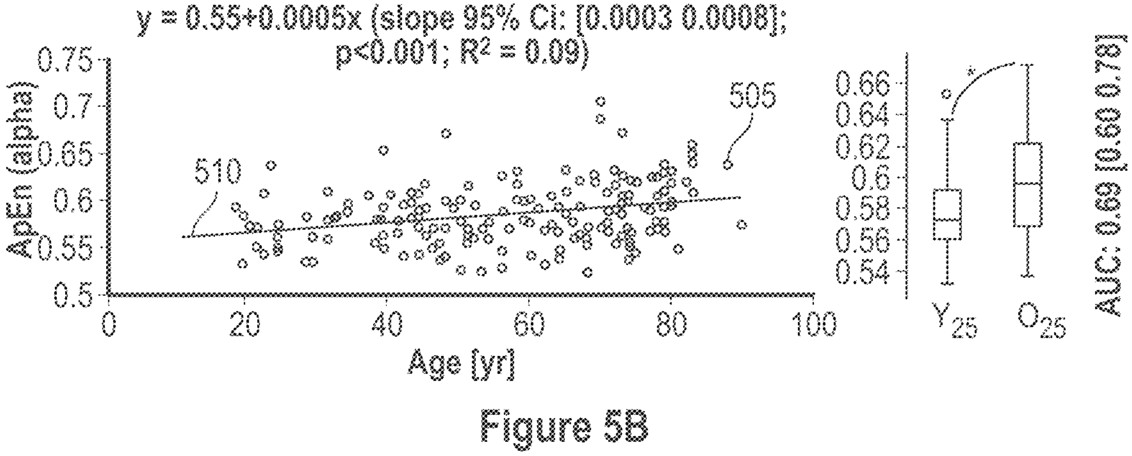
Figure 5C:
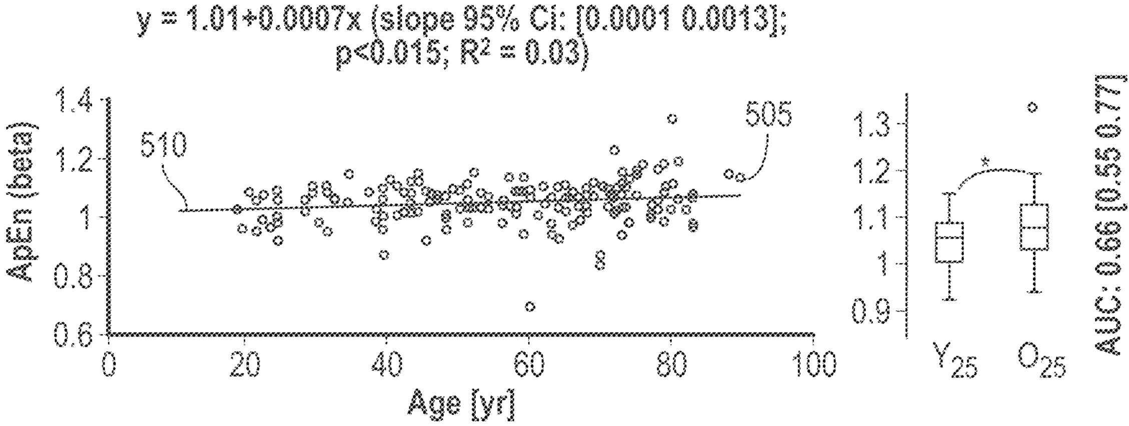
Figures 6A, 6B, 6C, 6D:
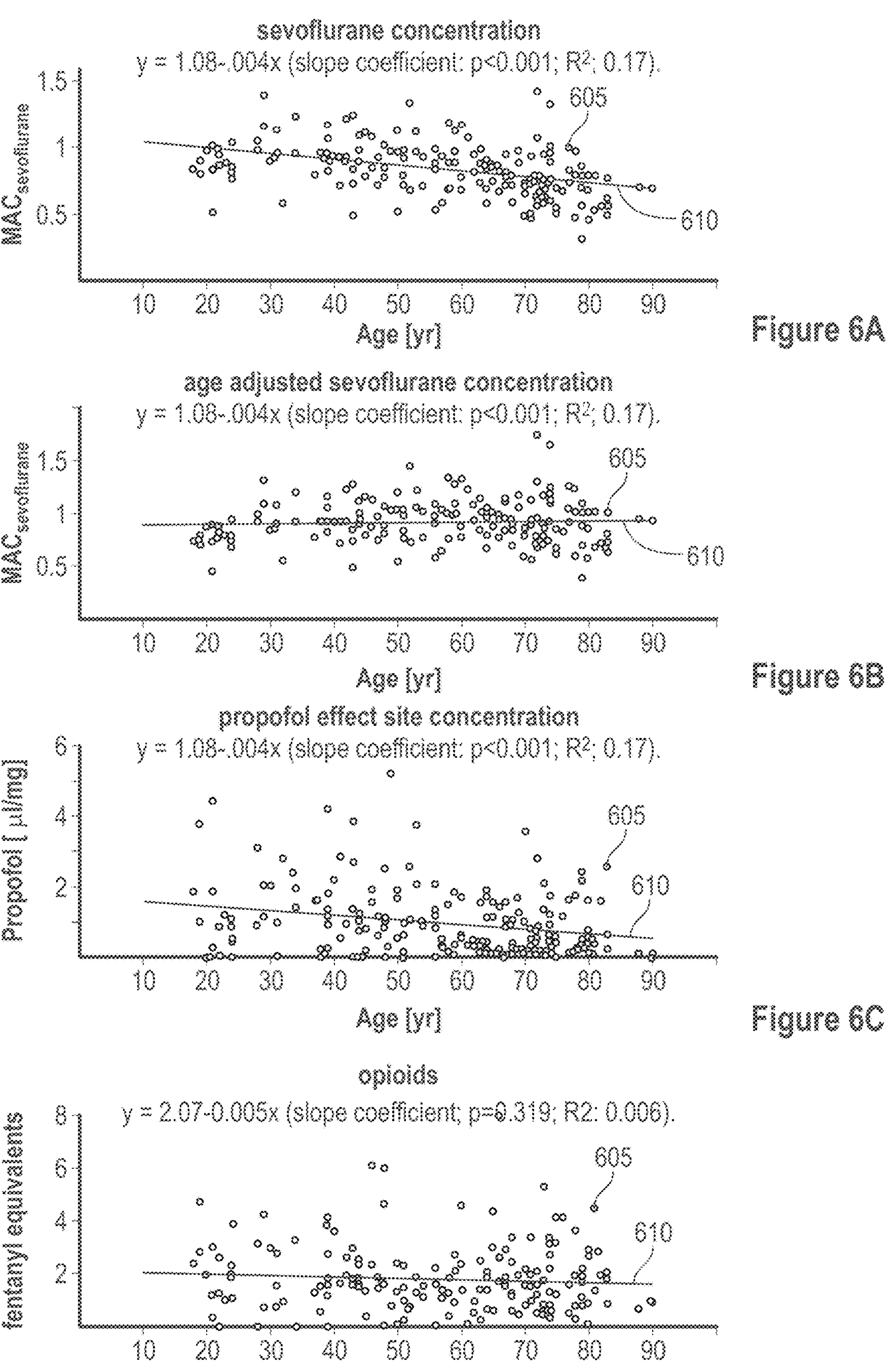
FIGS. 6A-6D are exemplary graphs illustrating drug dose to age relationships according to an exemplary embodiment of the present disclosure.

ApEn of all three frequency ranges increased with age as shown in FIGS. 5A-5C. The comparisons of ApEn for Y25 and O25 patients revealed a significant and moderate to strong effect of age in the 0.5-30 Hz range (e.g., p<0.001, AUC=0.76 [0.66 0.85]), in the EEG alpha range (e.g., p=0.002, AUC=0.69 [0.60 0.78]), as well as in the EEG beta range (e.g., p=0.007, AUC=0.66 [0.55 0.77]). The fact that ApEn, in contrast to PeEn, revealed an effect on the alpha-band possibly indicates a higher sensitivity of ApEn to lower frequencies. The ApEn (e.g., m=2, r=0.2 SD, τ=1) vs. age and corresponding youngest (e.g., Y25) vs. oldest (e.g., O25) quartile box plot is shown for the 0.5-30 Hz EEG range (See e.g., FIG. 5A), the EEG alpha range (See e.g., FIG. 5B), and the EEG beta range (See e.g., FIG. 5C). ApEn of the 0.5-30 Hz filtered EEG significantly (e.g., p<0.001, t-statistic: 4.87) increased with age. Age had a "fair" and significant (e.g., p<0.001; AUC=0.76 [0.66 0.85] 0.24 10.15 0.341) effect on ApEn as depicted in the comparison between Y25 (e.g., 0.83 [0.77 0.89]) and O25 (e.g., 0.93 [0.84 0.99]). ApEn of the alpha-band EEG significantly (e.g., p<0.001, t-statistic 4.18) increased with age. Age had a "poor"/"fair" and significant (e.g., p=0.002; AUC=0.69 [0.60 0.78] 0.31 10.22 0.401) effect on ApEn as depicted in the comparison between Y25 (e.g., 0.57 [0.56 0.59]) and O25 (e.g., 0.60 [0.57 0.62]). ApEn of the beta-band EEG significantly increased with age (e.g., p=0.015; AUC=0.66 [0.55 0.77]). Age had a "fair" and significant effect on ApEn as depicted in the comparison between O25 the oldest 25% (e.g., 1.08 [1.03 1.12]) and Y25 youngest 25% (e.g., 1.05 [1.00 1.08]) of the data set. In the regression plots, dots 505 represent the single patients and the line 510 represents the linear fit.

The entropic parameters did not undergo an age-related change in the slower dynamics, i.e., when applied to the EEG filtered to the delta and theta range. The detailed statistical parameters in Table 1 and the corresponding regression and box plots are provided in the FIGS. 10A-10D.

For example, FIGS. 10A-10D illustrate age induced-change of approximate entropy and permutation entropy in the slow dynamics, for example, the delta and theta range. ApEn decreased with age (e.g., p=0.029, t-statistic: −2.20), although the fit was quite poor with R2=0.03. The comparison of Y25 vs. O25 did not reveal a significant difference. ApEn did not show an aged-induced trend in the EEG theta range. Age did not influence PeEn, when applied to the EEG filtered to the delta range. Age did not influence PeEn, when applied to the EEG filtered to the theta range. In the exemplary regression plots, dots 1005 represent the single patients and line 1010 represents the linear fit.

Exemplary Surrogates

The surrogate analysis revealed a lower regression line for ApEn in the alpha and beta band as well as for PeEn in the beta band for the original signals. The phase randomization had no influence on the relative alpha- and beta band power. FIGS. 11A-11E show exemplary graphs illustrating the effect of phase randomization on relative alpha-power and beta-power according to an exemplary embodiment of the present disclosure. Results from the phase-randomized surrogate analysis of the parameter settings showing significant changes with age, for example, for the approximate entropy in the alpha-band (See e.g., FIG. 11A) and beta-band (See e.g., FIG. 11B), the permutation entropy in the beta-band (See e.g., FIG. 11C), as well as for the relative alpha-band (See e.g., FIG. 11D) and beta-band power (See e.g., FIG. 11E).

Exemplary Monitoring Parameters Show Age-Related Changes

The beta ratio and spectral entropy was used to estimate a possible influence of age on neurophysiological measures as implemented in commonly used monitoring systems. The BIS revealed a strong dependence on age as did the SpEnt for the 1.1 to 32 Hz and 1.1 to 47 Hz range. (See e.g., Table 1 and FIGS. 12A-12D)). The comparison of Y25 and O25 revealed significant and fair effects of age on beta ratio (e.g., p<0.001, AUC=0.73 [0.63 0.82]) and SpEnt (e.g., 1.1-32 Hz: p<0.001, AUC=0.79 [0.70 0.87]; 1.1-47 Hz: p<0.001, AUC=0.80 [0.71 0.88]. For the 0-8 to 32 Hz (e.g., p=0.202; AUC=0.58 [0.47 0.68]) or 47 Hz (e.g., p=0.161; AUC=0.58 [0.47 0.69]), a significant difference with age was not observed. These exemplary results indicate an influence of age on the (e.g., sub-) parameters that can be used to track neurophysiological changes in EEG-based monitoring systems which seems strongly dependent on the frequency range. For the sample of 168 patients, an increase of the recorded BIS with age (e.g., linear regression: p>0.001, t-statistic: 3.84; Y25 vs. O25: P=0.026, AUC=0.65 [0.52 0.76]) was observed.

Figures 12A, 12B, 12C, 12D:
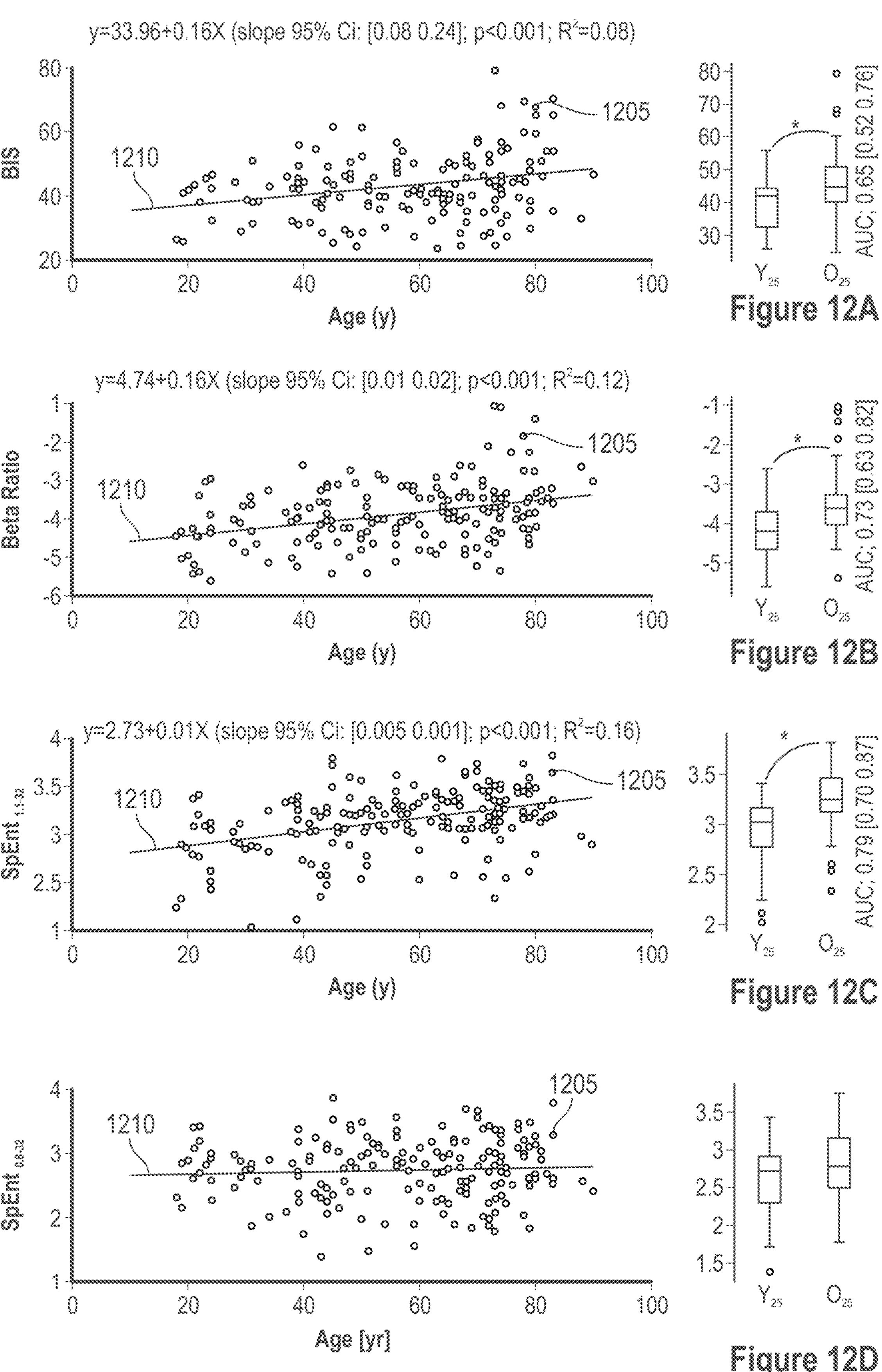
FIGS. 12A-12D are exemplary regression plots and box plots illustrating the dependence of bispectral index and SpEnt on age according to an exemplary embodiment of the present disclosure.

FIGS. 12A-12D show exemplary age induced-change of BIS (see, e.g., FIG. 12A), BetaRatio (see, e.g., FIG. 12B), and spectral entropy ("SpEnt") for the 0.8-32 Hz (see, e.g., FIG. 12C) and the 1.1-32 Hz range (see, e.g., FIG. 12D). As shown in FIG. 12A, BIS values increased with age (e.g., p<0.001, t-statistic 3.84) and age had a "poor" but significant (e.g., p=0.026, AUC=0.65 [0.52 0.76] 0.35 10.24 0.481) effect as depicted in the Y25 vs. O25 boxplot. The beta ratio as proxy for the bispectral index increased (e.g., p<0.001, t-statistic 5.00) with age. Age had a "fair" (e.g., AUC=0.73 [0.63 0.82] 0.71 [0.60 0.81]) and significant (e.g., p<0.001) effect on beta ratio as depicted in the Y25 vs. O25 boxplot. The beta ratio as subparameter of the BIS increased (e.g., p<0.001, t-statistic: 5.00) with age. Age had a "fair" and significant (e.g., p<0.001, AUC=0.73 [0.63 0.82] 0.27 10.18 0.371) effect on beta ratio as depicted in the Y25 vs. O25 boxplot. SpEnt for the 1.1-32 Hz range as proxy for the state entropy index from the Entropy Module increased (e.g., p<0.001, t-statistic: 5.81) with age. Age had a "fair" to "good" and significant (e.g., p<0.001, AUC=0.79 [0.70 0.87]0.21 [0.13 0.30]) effect as depicted in the Y25 vs. O25 boxplot. SpEnt for the 0.8-32 Hz range as proxy for the state entropy index from did not show a significant influence of age on SpEnt (e.g., p=0.433, t-statistic: 0.79) with age. Age no effect (e.g., p=0.201, AUC=0.58 [0.47 0.68]0.42 [0.32 0.53]) effect as depicted in the Y25 vs. O25 boxplot. In the regression plots, dots 1205 represent the single patients and th lines 1210 represent the linear fit.

Further Exemplary Detailed Description

Exemplary results show that age-dependent changes in EEG characteristics during general anesthesia extend beyond a mere decrease in EEG amplitude. Exemplary demonstrable changes in PSD of EEG recorded under general anesthesia have been reported by other groups. (See, e.g., References 8 and 9). The absolute power can decrease with age in every frequency range. After normalization, it was determined that delta oscillations contributed less to total power with age, while beta oscillations (e.g., high) contributed more. The change in the 1/f characteristics as revealed by the FOOOF analysis confirm this finding. A significant change was not observed in the relative power in the specific bands, but the additional usage of entropic parameters revealed that these parameters can be capable of tracking subtler changes in the oscillatory composition of the EEG that may not be detected by PSD-based approaches, also in the alpha- and beta band. The entropic parameters can be used to analyze additional content in the signal as shown by surrogate analysis. The higher entropies in the surrogates can indicate a loss in deterministic signal properties. (See, e.g., Reference 35). The exemplary monitoring parameters BIS, BetaRatio, and spectral entropy were also affected by age, a finding highlighting that age adjustments can be considered for monitoring.

Exemplary Influence of Age on EEG Amplitude and PSD

Reductions in grey matter, including cortical thinning (See, e.g., References 36-40) or a decrease in skull conductance (See, e.g., Reference 41) with age can cause a decrease in EEG amplitude, and hence lower PSD. Additionally, the EEG amplitude can also depend (e.g., at least in part) on neuronal synchrony, but it can be unknown at present to what extent this can be altered by aging. (See, e.g., Reference 42).

Exemplary Age Influences EEG Spectral Power

Exemplary PSD analyses can be in line with previously published findings, i.e., PSD decreases with age. (See, e.g., Reference 9). It can be possible to add to these results the more uniformly distributed nPSD that can be reflected by a flatter (e.g., aperiodic) 1/f slope. Changes in relative band power for propofol anesthesia and other groups for NREM sleep have been shown. (See, e.g., References 8, 12, and 43). Age-related cortical activation during NREM sleep seems to increase relative beta power (See, e.g., Reference 12) a scenario that can be possible for exemplary findings under general anesthesia as well. Further, aged women had lower relative EEG delta-band and higher beta-band power during wakefulness and REM sleep compared to a middle-aged group. (See, e.g., Reference 44). In general, there can be a number of potential explanations that can cause the observed shift in the relative power spectrum. An increase of neural noise can be one of them. Older test subjects had a flatter 1/f slope during visual tasks, due to increased neural noise.

(See, e.g., References 42 and 45). This increase does not have to represent a more aroused brain state since recent research found increased higher beta-frequencies to be associated with poorer memory test outcome in geriatric women. (See, e.g., Reference 46). Volunteers with eyes closed exhibited higher beta-coherence with age, indicative of higher synchrony in this frequency range. (See, e.g., Reference 47). But, besides a possible increase in neural noise, the changes in spatiotemporal filtering properties can be due to a change of age-related, physiological changes affecting the cortex (See, e.g., Reference 40) for instance the extracellular space, which can act as 1/f filter. (See, e.g., Reference 48). Further, age, and the decline in EEG power can also reduce the signal to noise ratio as, for example, shown in experiments with event-related potentials. (See, e.g., Reference 49). Exemplary findings can either reflect increased cortical neural noise, for example, spiking not correlated to oscillatory activity in the elderly brain, the age-induced change of physiological 1/f filtering properties, or changes in the signal to noise ratio of the EEG with age, or a combination of these factors. The exemplary observational study was not designed to closely investigate the cause for the flatter slope. The exemplary results further showed that the relative alpha and beta-band power was not affected by age. Entropic measures in the time domain, like approximate entropy and permutation entropy, provide information separate from spectral features. (See, e.g., References 15-17, and 27). An understanding of both spectral and entropic features can broaden exemplary clinical model of estimations regarding consciousness in patients under general anesthesia.

Exemplary Older Patients Express Higher Signal Entropy

Exemplary findings showed increasing approximate entropy and permutation entropy (e.g., except in the alpha-band) values with age. The exemplary results of approximate entropy and permutation entropy differ to some degree, because both parameters can target different EEG characteristics. (See, e.g., Reference 50). Permutation entropy can be regarded as superior to approximate entropy in distinguishing conscious from unconscious EEG (See, e.g., Reference 16, 17, and 51) while approximate entropy performs better than permutation entropy in tracking different levels of anesthesia. (See, e.g., Reference 17). These differences can be in accordance with the strong effect of age on permutation entropy in the high frequencies (e.g., beta-band), as well as the ability of approximate entropy to identify differences in the alpha band—where permutation entropy showed no contrast. The age-related increase in entropic measures can apply to other vigilance states and encephalographic modalities as well: in a magnetoencephalography study, permutation entropy increased with age in volunteers that were awake with their eyes closed. (See, e.g., Reference 52). In general, the increase of entropic measures with age probably can reflect the effect on the 1/f slope by indicating a more uniform distribution of ordinal EEG patterns (e.g., PeEn), and a decreased signal predictability (e.g., ApEn) in the elderly. An association between permutation entropy (e.g., for m=3) and the spectral centroid of the (e.g., weighted) PSD was recently described. (See, e.g., Reference 53). This proposition can add a general link between spectral analytical approaches and permutation entropy, such that ordinal irregularity can become usable as a proxy for changes in the oscillatory EEG composition.

This link can still be missing for approximate entropy, though. But these measures can track deterministic properties in the signal, in contrast to PSD measures. Although other settings of permutation entropy can be used to track age-related changes with higher precision, the underlying cause for that may be unknown. Since using lags of $\tau>1$ can lead to unintended distortions in the signal (See, e.g., Reference 53) permutation entropy with $\tau=1$ to EEG filtered to the different frequency bands was applied. The exemplary analyses demonstrate the sensitivity of entropic measures to subtle changes in the EEG.

Exemplary Reasons for Altered EEG Characteristics

There is evidence that the aged brain reacts to general (e.g., sevoflurane) anesthesia differently than the young brain. In young brains, usually, a peak in the EEG alpha range develops under general anesthesia (See, e.g., Reference 34) as a marker of adequate anesthesia. This peak in the EEG alpha-band, as well as strong interhemispheric EEG alpha-band coherence (See, e.g., Reference 34) can be associated with thalamocortical pacemaker cells and their activity spreading to the cortex. (See, e.g., Reference 54). Older and cognitively impaired patients express lower alpha power and alpha coherence during general anesthesia. (See, e.g., References 9, 10, and 55). An influence of age was not observed using the relative alpha-band power, similar to findings of age related differences in relative alpha power only at very profound levels of propofol anesthesia. (See, e.g., Reference 8). Thus, the described decrease in alpha power can be due to the general decrease in EEG amplitude with age.

Although an influence of age in relative alpha-band power in the results was not observed, approximate entropy of the alpha-band revealed a significant change. Because strong and synchronous (e.g., low ApEn) alpha oscillations can correlate with good cognitive function and better outcomes after general anesthesia (See, e.g., References 10, 56, and 57) this parameter can be useful to identify patients with a 'frail' brain using EEG recordings during general anesthesia in the future. For both entropic parameters, changes in the EEG beta range were observed. This frequency range can be associated with an activated cortex and intracortical as well as corticocortical information processing. (See, e.g., References 54 and 58). Thus, exemplary findings of a flatter 1/f slope can reflect a state of higher cortical activation in the elderly, or a higher influence of noise. During visual tasks the flatter 1/f slope can represent a decoupling of cortical population spiking activity from an oscillatory regimen. (See, e.g., Reference 42). Furthermore, findings from sleep research indicate that the EEG of older subjects during sleep can be closer to the wake state than in middle-aged to young subjects. (See, e.g., Reference 44). At the same time, age seems to affect thalamocortical regulatory mechanisms during sleep as expressed by lower sleep spindle density, duration, and amplitude. (See, e.g., Reference 59). In general, the EEG of older patients can have a smaller dynamic range. During the awake state, the EEG can be slower in the older population (See, e.g., Reference 8) and it shows increased relative beta power during general anesthesia. Thus, the aged brain may not be capable of expressing activated or synchronized activity to the same degree that the young adult brain can be capable of. Therefore, a difference between chronologic vs. functional brain age can be considered to reveal functional-age-related differences in the EEG in more detail. Young patients with potential for having a frail brain can express EEG activity typical for an old patient. (See, e.g., Reference 55). Furthermore, (e.g., mild) cognitive impairments like early-stage Alzheimer's seem to change the EEG architecture in a similar fashion as aging. (See, e.g., Reference 60).

Consequently, exemplary results indicate an influence of age on the indices of commonly used EEG monitors (e.g., BIS and GE Entropy) towards a lower dose. But the presented exemplary BIS values may not correlate with exemplary analyzed EEG segments because of a considerable time delay of up to 60. (See, e.g., References 61 and 62). Still, recent findings indicate higher BIS in older adults; thus, emphasizing exemplary results. (See, e.g., Reference 63). At least some of the commercially available monitors were developed using data from rather young adult subjects. (See, e.g., Reference 64). A study found that at the propofol-induced loss of consciousness, older patients expressed higher BIS and state entropy values, projecting a "more awake" EEG by means of the indices. (See, e.g., Reference 65). These and exemplary findings can indicate that future EEG-based "depth of anesthesia" monitoring systems can account for patient age, or use parameters not affected by age. In exemplary data limited to EEG during unstimulated unconsciousness, relative alpha and beta power did not change with age but showed considerable variability. Thus, a use for monitoring purposes can also be examined.

Figure 13:
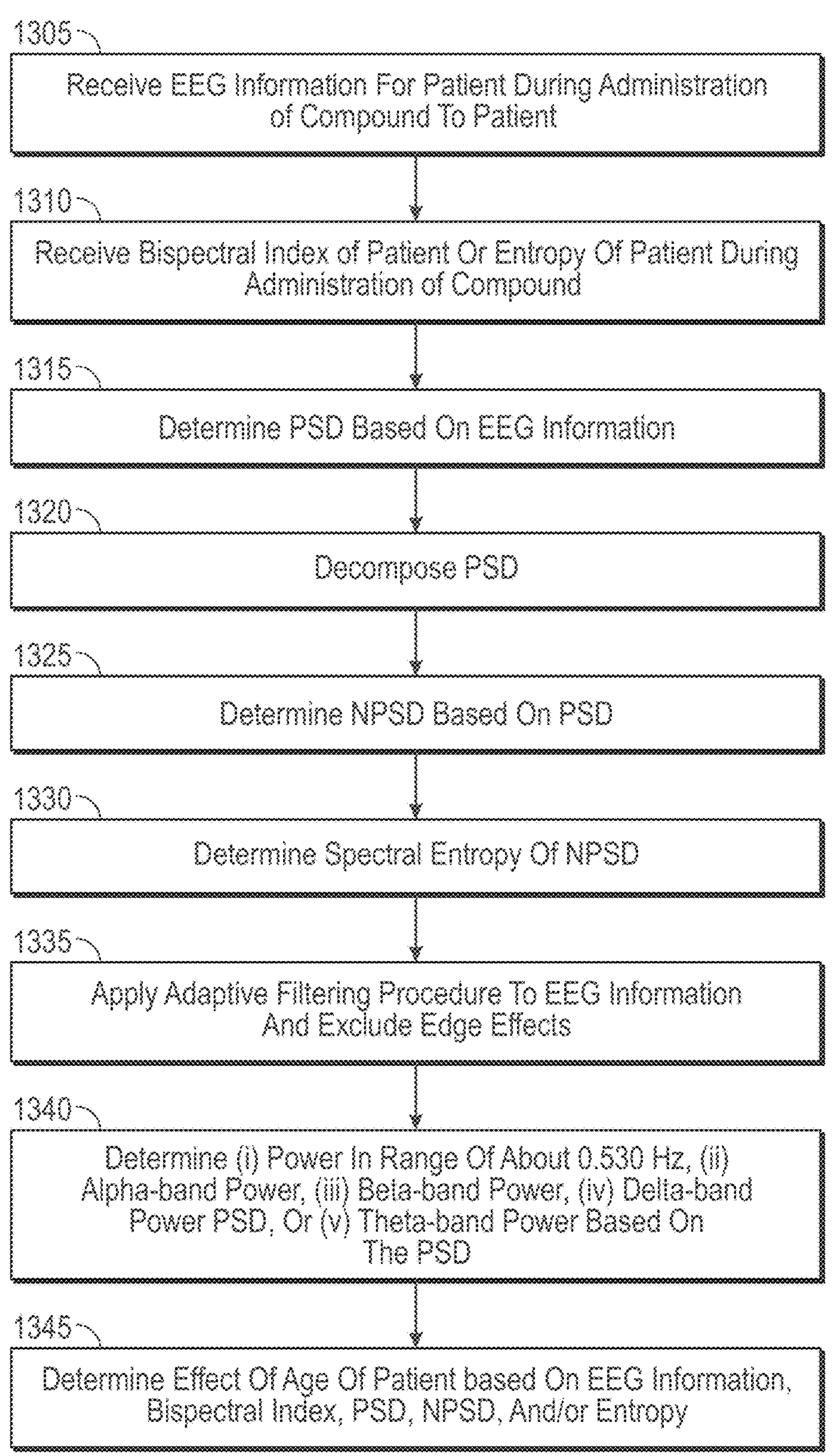
FIG. 13 is an exemplary flow diagram of a method for determining an effect of an age of a patient during an administration of a compound according to an exemplary embodiment of the present disclosure.
Figure 14:
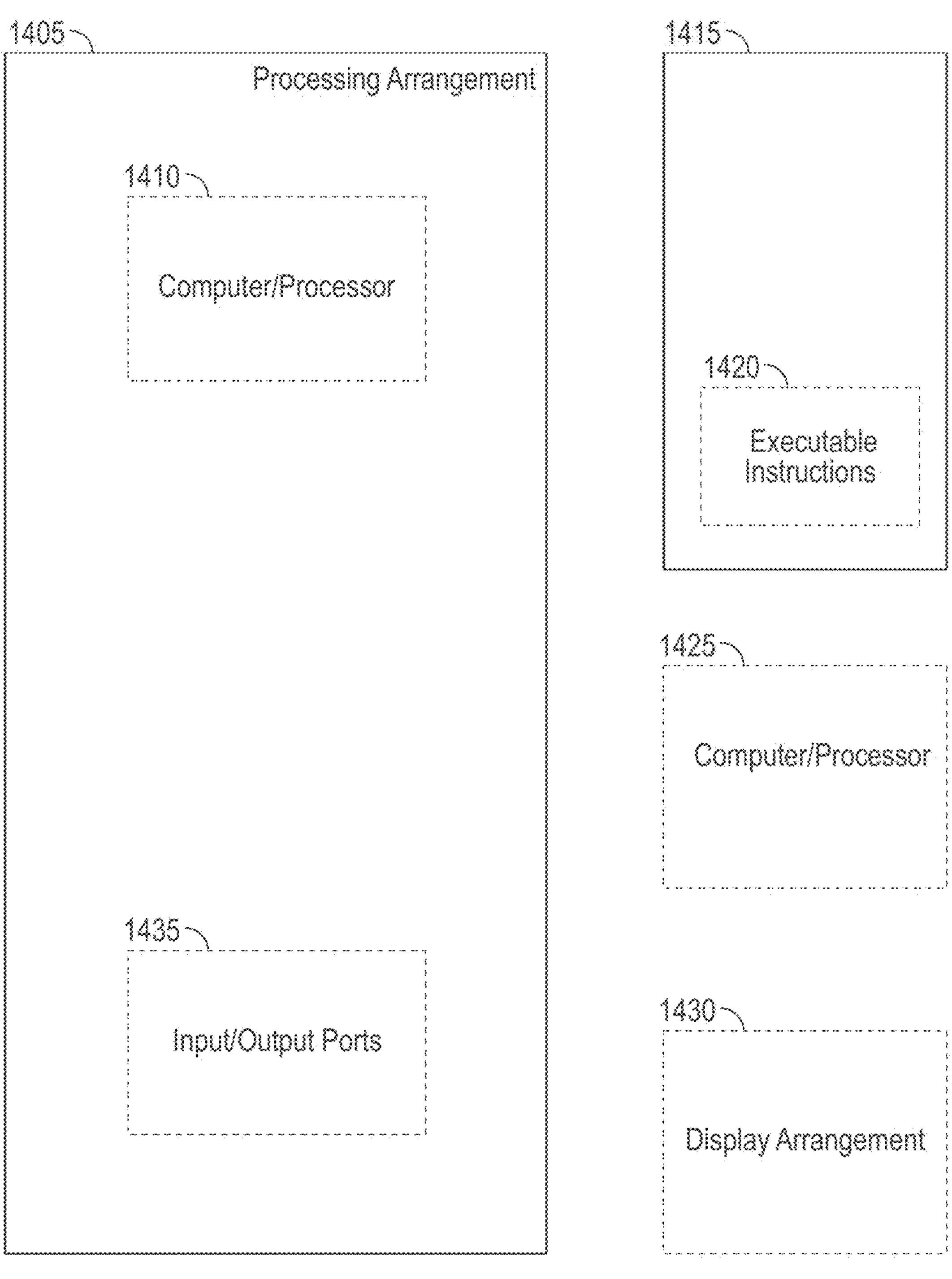
FIG. 14 is an illustration of an exemplary block diagram of an exemplary system in accordance with certain exemplary embodiments of the present disclosure.

FIG. 13 shows an exemplary flow diagram of a method 1300 for determining an effect of an age of a patient during an administration of a compound according to an exemplary embodiment of the present disclosure. For example, at procedure 1305, EEG information for the patient can be received during the administration of the compound to the patient. At procedure 1310, a bispectral index of the patient or an entropy of the patient during the administration of the compound can be received. At procedure 1315, a PSD can be determined based on the EEG information, which can be decomposed at procedure 1320. At procedure 1325, the nPSD can be determined based on the PSD. At procedure 1330, a spectral entropy of the nPSD can be determined. At procedure 1335, an adaptive filtering procedure can be applied to the EEG information, which can exclude edge effects, at procedure 1340, (i) a power in a range of about 0.530 Hz, (ii) an alpha-band power, (iii) a beta-band power, (iv) a delta-band power PSD, or (v) a theta-band power based on the PSD can be determined. At procedure 1345, the effect of the age of the patient can be determined based on the EEG information, the bispectral index, the PSD, the nPSD, and/or the entropy FIG. 14 shows a block diagram of an exemplary embodiment of a system according to the present disclosure. For example, exemplary procedures in accordance with the present disclosure described herein can be performed by a processing arrangement and/or a computing arrangement (e.g., computer hardware arrangement) 1405. Such processing/computing arrangement 1405 can be, for example entirely or a part of, or include, but not limited to, a computer/processor 1410 that can include, for example one or more microprocessors, and use instructions stored on a computer-accessible medium (e.g., RAM, ROM, hard drive, or other storage device).

As shown in FIG. 14, for example a computer-accessible medium 1415 (e.g., as described herein above, a storage device such as a hard disk, floppy disk, memory stick, CD-ROM, RAM, ROM, etc., or a collection thereof) can be provided (e.g., in communication with the processing arrangement 1405). The computer-accessible medium 1415 can contain executable instructions 1420 thereon. In addition or alternatively, a storage arrangement 1425 can be provided separately from the computer-accessible medium 1415, which can provide the instructions to the processing arrangement 1405 so as to configure the processing arrangement to execute certain exemplary procedures, processes, and methods, as described herein above, for example.

Further, the exemplary processing arrangement 1405 can be provided with or include an input/output ports 1435, which can include, for example a wired network, a wireless network, the internet, an intranet, a data collection probe, a sensor, etc. As shown in FIG. 14, the exemplary processing arrangement 1405 can be in communication with an exemplary display arrangement 1430, which, according to certain exemplary embodiments of the present disclosure, can be a touch-screen configured for inputting information to the processing arrangement in addition to outputting information from the processing arrangement, for example. Further, the exemplary display arrangement 1430 and/or a storage arrangement 1425 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entireties:

1. Delafuente J C: The silver tsunami is coming: will pharmacy be swept away with the tide? Am. J. Pharm. Educ. 2009; 73: 1.
2. Etzioni D A, Liu R I, Maggard M A, Ko C Y: The aging population and its impact on the surgery workforce. Ann. Surg. 2003; 238: 170.
3. Fritz B A, Kalarickal P L, Maybrier H R, Muench M R, Dearth D, Chen Y, Escallier K E, Ben Abdallah A, Lin N, Avidan M S: Intraoperative Electroencephalogram Suppression Predicts Postoperative Delirium. Anesth. Analg. 2016; 122: 234-42.
4. Radtke F, Franck M, Hagemann L, Seeling M, Wernecke K, Spies C: Risk factors for inadequate emergence after anesthesia: emergence delirium and hypoactive emergence. Minerva Anestesiol. 2010; 76: 394-403.
5. Watson P L, Shintani A K, Tyson R, Pandharipande P P, Pun B T, Ely E W: Presence of electroencephalogram burst suppression in sedated, critically ill patients is associated with increased mortality. Crit. Care Med. 2008; 36: 3171-7.
6. Radtke F, Franck M, Lendner J, Kruger S, Wernecke K, Spies C: Monitoring depth of anaesthesia in a randomized trial decreases the rate of postoperative delirium but not postoperative cognitive dysfunction. Br J Anaesth 2013; 110: i98-i105.

7. Wildes T S, Mickle A M, Ben Abdallah A, Maybrier H R, Oberhaus J, Budelier T P, Kronzer A, McKinnon S L, Park D, Tones B A, Graetz T J, Emmert D A, Palanca B J, Goswami S, Jordan K, Lin N, Fritz B A, Stevens T W, Jacobsohn E, Schmitt E M, Inouye S K, Stark S, Lenze E J, Avidan M S: Effect of Electroencephalography-Guided Anesthetic Administration on Postoperative Delirium Among Older Adults Undergoing Major Surgery: The ENGAGES Randomized Clinical Trial. JAMA 2019; 321: 473-483.
8. Schultz A, Grouven U, Zander I, Beger F A, Siedenberg M, Schultz B: Age-related effects in the EEG during propofol anaesthesia. Acta Anaesthesiol Scand 2004; 48: 27-34.
9. Purdon P, Pavone K, Akeju O, Smith A, Sampson A, Lee J, Zhou D, Solt K, Brown E: The Ageing Brain: Age-dependent changes in the electroencephalogram during propofol and sevoflurane general anaesthesia. Br J Anaesth 2015; 115: i46-i57.
10. Giattino C, Gardner J, Sbahi F, Roberts K, Cooter M, Moretti E, Browndyke J, Mathew J, Woldorff M, Berger M: Intraoperative Frontal Alpha-Band Power Correlates with Preoperative Neurocognitive Function in Older Adults. Front. Syst. Neurosci. 2017; 11.
11. Polich J: EEG and ERP assessment of normal aging. Electroencephalography and Clinical Neurophysiology/Evoked Potentials Section 1997; 104: 244-256.
12. Carrier J, Land S, Buysse D J, Kupfer D J, Monk T H: The effects of age and gender on sleep EEG power spectral density in the middle years of life (ages 20-60 years old). Psychophysiology 2001; 38: 232-242.
13. Bandt C, Pompe B: Permutation Entropy: A Natural Complexity Measure for Time Series. Phys. Rev. Lett. 2002; 88: 174102.
14. Pincus S M: Approximate entropy as a measure of system complexity. Proc. Natl. Acad. Sci. U.S.A 1991; 88: 2297-2301.
15. Olofsen E, Sleigh J W, Dahan A: Permutation entropy of the electroencephalogram: a measure of anaesthetic drug effect. Br J Anaesth 2008; 101: 810-21.
16. Jordan D, Stockmanns G, Kochs E F, Pilge S, Schneider G: Electroencephalographic Order Pattern Analysis for the Separation of Consciousness and Unconsciousness: An Analysis of Approximate Entropy, Permutation Entropy, Recurrence Rate, and Phase Coupling of Order Recurrence Plots. Anesthesiology 2008; 109: 1014-1022.
17. Schneider G, Jordan D, Schwarz G, Bischoff P, Kalkman C J, Kuppe H, Rundshagen I, Omerovic A, Kreuzer M, Stockmanns G, Kochs EF: Monitoring depth of anesthesia utilizing a combination of electroencephalographic and standard measures. Anesthesiology 2014; 120: 819-28.
18. Rampil I J: A Primer for EEG Signal Processing in Anesthesia. Anesthesiology 1998; 89: 9801002.
19. Viertio-Oja H, Maja V, Sarkela M, Talja P, Tenkanen N, Tolvanen-Laakso H, Paloheimo M, Vakkuri A, Yli-Hankala A, Merilainen P: Description of the Entropy algorithm as applied in the Datex-Ohmeda S/5 Entropy Module. Acta Anaesthesiol Scand 2004; 48: 154-61.
20. Hight D, Voss L J, Garcia P S, Sleigh J: Changes in Alpha Frequency and Power of the Electroencephalogram during Volatile-Based General Anesthesia. Front. Syst. Neurosci. 2017; 11
21. McKay I D, Voss L J, Sleigh J W, Barnard J P, Johannsen E K: Pharmacokinetic-pharmacodynamic modeling the hypnotic effect of sevoflurane using the spectral entropy of the electroencephalogram. Anesth. Analg. 2006; 102: 91-97.
22. Mapleson W: Effect of age on MAC in humans: a meta-analysis. Br J Anaesth 1996; 76: 179-185.
23. Mazoit J X, Butscher K, Samii K: Morphine in postoperative patients: pharmacokinetics and pharmacodynamics of metabolites. Anesth. Analg. 2007; 105: 70-78.
24. Shafer S L, Varvel J R: Pharmacokinetics, pharmacodynamics, and rational opioid selection. Anesthesiology 1991; 74: 53-63.
25. Wiczling P, Bienert A, Sobczyr9iski P, Hartmann-Sobczyr9iska R, Bieda K, Marcinkowska A, Malatyr9iska M, Kaliszan R, Grześkowiak E: Pharmacokinetics and pharmacodynamics of propofol in patients undergoing abdominal aortic surgery. Pharmacol. Rep. 2012; 64: 113-122.
26. Haller M, Donoghue T, Peterson E, Varma P, Sebastian P, Gao R, Noto T, Knight R T, Shestyuk A, Voytek B: Parameterizing neural power spectra. bioRxiv 2018: 299859.
27. Bruhn J, Ropcke H, Hoeft A: Approximate Entropy as an Electroencephalographic Measure of Anesthetic Drug Effect during Desflurane Anesthesia. Anesthesiology 2000; 92: 715-726.
28. Nicolaou N, Houris S, Alexandrou P, Georgiou J: Entropy measures for discrimination of 'awake' Vs 'anaesthetized' state in recovery from general anesthesia. Conf Proc IEEE Eng Med Biol Soc 2011; 2011: 2598-601.
29. Shannon C: A Mathematical Theory of Communication. Bell Syst. Tech. J 1948; 27: (379-423):623-56.
30. Kreuzer M: EEG Based Monitoring of General Anesthesia: Taking the Next Steps. Front. Comput. Neurosci. 2017; 11: 56.
31. Goldberger A, Amaral L, Glass L, Hausdorff J, Ivanov P, Mark R, Mietus J, Moody G, Peng C, Stanley H: PhysioBank, PhysioToolkit, and PhysioNet: Components of a New Research Resource for Complex Physiologic Signals. Circulation 2000; 101: e215-e220.
32. Schneider G, Schöniger S, Kochs E: Does bispectral analysis add anything but complexity? BIS sub-components may be superior to BIS for detection of awareness. Br J Anaesth 2004; 93: 596-597.
33. Hentschke H, Stüttgen M C: Computation of measures of effect size for neuroscience data sets. Eur. J. Neurosci. 2011; 34: 1887-1894.
34. Akeju O, Westover M B, Pavone K J, Sampson A L, Hartnack K E, Brown E N, Purdon P L: Effects of sevoflurane and propofol on frontal electroencephalogram power and coherence. Anesthesiology 2014; 121: 990-998.
35. Jordan D, Stockmanns G, Kochs E F, Schneider G: Is Detection of Different Anesthetic Levels Related to Nonlinearity of the Electroencephalogram?, 4th European Conference of the International Federation for Medical and Biological Engineering. Edited by Sloten J, Verdonck P, Nyssen M, Haueisen J, Springer Berlin Heidelberg, 2009, pp 335-339.
36. Raz N, Lindenberger U, Rodrigue K M, Kennedy K M, Head D, Williamson A, Dahle C, Gerstorf D, Acker J D: Regional brain changes in aging healthy adults: General trends, individual differences and modifiers. Cereb. Cortex 2005; 15: 1676-1689.
37. Salat D H, Buckner R L, Snyder A Z, Greve D N, Desikan R S R, Busa E, Morris J C, Dale A M, Fischl B: Thinning of the cerebral cortex in aging. Cereb. Cortex 2004; 14: 721-730.
38. Fjell A M, Walhovd K B, Fennema-Notestine C, McEvoy L K, Hagler D J, Holland D, Brewer J B, Dale A M:

One-Year Brain Atrophy Evident in Healthy Aging. J. Neurosci. 2009; 29: 15223-15231.

39. Fjell A M, Westlye L T, Amlien I, Espeseth T, Reinvang I, Raz N, Agartz I, Salat D H, Greve D N, Fischl B: High consistency of regional cortical thinning in aging across multiple samples. Cereb. Cortex 2009: bhn232.

40. Thompson P M, Hayashi K M, Dutton R A, CHIANG M C, Leow A D, Sowell E R, De Zubicaray G, Becker J T, Lopez O L, Aizenstein H J: Tracking Alzheimer's disease. Ann. N.Y. Acad. Sci. 2007; 1097: 183-214.

41. Hoekema R, Wieneke G H, Leijten F S S, van Veelen C W M, van Rijen P C, Huiskamp G J M, Ansems J, van Huffelen A C: Measurement of the conductivity of skull, temporarily removed during epilepsy surgery. Brain Topogr. 2003; 16: 29-38.

42. Voytek B, Kramer M A, Case J, Lepage K Q, Tempesta Z R, Knight R T, Gazzaley A: Age-Related Changes in 1/f Neural Electrophysiological Noise. J Neurosci 2015; 35: 13257-65.

43. Chinoy E D, Frey D J, Kaslovsky D N, Meyer F G, Wright K P: Age-related changes in slow wave activity rise time and NREM sleep EEG with and without zolpidem in healthy young and older adults. Sleep Med. 2014; 15: 1037-1045.

44. Bruce E N, Bruce M C, Vennelaganti S: Sample entropy tracks changes in EEG power spectrum with sleep state and aging. J. Clin. Neurophysiol. 2009; 26: 257.

45. Dave S, Brothers T A, Swaab T Y: 1/f neural noise and electrophysiological indices of contextual prediction in aging. Brain Research 2018; 1691: 34-43.

46. Kaiser A K, Doppelmayr M, Iglseder B: EEG beta 2 power as surrogate marker for memory impairment: a pilot study. Int. Psychogeriatr. 2017; 29: 1515-1523.

47. Vysata O, Kukal J, Prochazka A, Pazdera L, Simko J, Valis M: Age-related changes in EEG coherence. Neurol. Neurochir. Pol. 2014; 48: 35-38.

48. Bedard C, Kroger H, Destexhe A: Does the 1/f frequency scaling of brain signals reflect self-organized critical states? Phys. Rev. Lett. 2006; 97: 118102.

49. Hammerer D, Li S C, Volkle M, Muller V, Lindenberger U: A lifespan comparison of the reliability, test-retest stability, and signal-to-noise ratio of event-related potentials assessed during performance monitoring. Psychophysiology 2013; 50: 111-23.

50. Keller K, Mangold T, Stolz I, Werner J: Permutation Entropy: New Ideas and Challenges. Entropy 2017; 19: 134.

51. Brown E N, Lydic R, Schiff N D: General Anesthesia, Sleep, and Coma. N. Engl. J. Med. 2010; 363: 2638-2650.

52. Shumbayawonda E, Fernandez A, Hughes M P, Abásolo D: Permutation Entropy for the Characterisation of Brain Activity Recorded with Magnetoencephalograms in Healthy Ageing. Entropy 2017; 19: 141.

53. Berger S, Schneider G, Kochs E F, Jordan D: Permutation Entropy: Too Complex a Measure for EEG Time Series? Entropy 2017; 19: 692.

54. John E R, Prichep L S: The Anesthetic Cascade: A Theory of How Anesthesia Suppresses Consciousness. Anesthesiology 2005; 102: 447-471.

55. Kreuzer M, Whalin M K, Hesse S D, Riso M A, Garcia P S: Anesthetic Management of a Patient With Multiple Previous Episodes of Postanesthesia Care Unit Delirium: A Case Report. A&A Case Reports 2017; 8: 311-315.

56. Chander D, Garcia P S, MacColl J N, Illing S, Sleigh J W: Electroencephalographic variation during end maintenance and emergence from surgical anesthesia. PloS one 2014; 9: e106291.

57. Hesse S, Kreuzer M, Hight D, Gaskell A, Devari P, Singh D, Taylor N, Whalin M, Lee S, Sleigh J: Association of electroencephalogram trajectories during emergence from anaesthesia with delirium in the post-anaesthesia care unit: an early sign of postoperative complications. Br J Anaesth 2019; 122: 622-634.

58. Bassett D S, Bullmore E T, Meyer-Lindenberg A, Apud J A, Weinberger D R, Coppola R: Cognitive fitness of cost-efficient brain functional networks. Proc. Natl. Acad. Sci. U.S.A 2009; 106: 1174711752.

59. Crowley K, Trinder J, Kim Y, Carrington M, Colrain I M: The effects of normal aging on sleep spindle and K-complex production. Clin. Neurophysiol. 2002; 113: 1615-1622.

60. Frantzidis C A, Ladas A, Diamantoudi M D, Semertzidou A, Grigoriadou E, Tsolaki A, Liapi D, Papadopoulou A, Kounti F, Vivas A B: What are the symbols of Alzheimer? A permutation entropy based symbolic analysis for the detection of early changes of the electroencephalographic complexity due ue to mild Alzheimer, Bioinformatics & Bioengineering (BIBE), 2012 IEEE 12th International Conference on, IEEE, 2012, pp 282-287.

61. Pilge S, Zanner R, Schneider G, Blum J, Kreuzer M, Kochs E: Time Delay of Index Calculation: Analysis of Cerebral State, Bispectral, and Narcotrend Indices. Anesthesiology 2006; 104: 488-494.

62. Zanner R, Pilge S, Kochs E F, Kreuzer M, Schneider G: Time delay of electroencephalogram index calculation: analysis of cerebral state, bispectral, and Narcotrend indices using perioperatively recorded electroencephalographic signals. Br J Anaesth 2009; 103: 394-399.

63. Ni K, Cooter M, Gupta D K, Thomas J, Hopkins T J, Miller T E, James M L, Kertai M D, Berger M: Paradox of age: older patients receive higher age-adjusted minimum alveolar concentration fractions of volatile anaesthetics yet display higher bispectral index values. Br J Anaesth 2019; 123: 288-297.

64. Prichep L, Gugino L, John E, Chabot R, Howard B, Merkin H, Tom M, Wolter S, Rausch L, Kox W: The Patient State Index as an indicator of the level of hypnosis under general anaesthesia. Br J Anaesth 2004; 92: 393-399.

65. Lysakowski C, Elia N, Czarnetzki C, Dumont L, Haller G, Combescure C, Tramer M R: Bispectral and spectral entropy indices at propofol-induced loss of consciousness in young and elderly patients. Br J Anaesth 2009; 103: 387-93.

66. Dundee J, Robinson F P, McCollum J, Patterson C: Sensitivity to propofol in the elderly. Anaesthesia 1986; 41: 482-485.

67. Teplan M: Fundamentals of EEG measurement. Meas. Sci. Rev. 2002; 2: 1-11.

What is claimed is:

1. A non-transitory computer-accessible medium having stored thereon computer-executable instructions for determining a functional brain age of a patient during an administration of a compound, wherein, when a computer arrangement executes the instructions, the computer arrangement is configured to perform procedures comprising:

receiving electroencephalographic (EEG) information for a patient during the administration of the compound to the patient;

receiving an entropy of the EEG information for the patient during the administration of the compound;

determining a functional brain age of the patient based on the entropy; and adjusting the administration of the compound based on the determined functional brain age of the patient.

2. The computer-accessible medium of claim 1, wherein the compound includes an anesthesia.

3. The computer-accessible medium of claim 2, wherein the anesthesia includes at least one of (i) sevoflurane, (ii) isoflurane, (iii) dexmedetomidine, (iv) propofol, (v) etomidate, (vi) desflurane, or (vii) a combination of ketamine and nitrous oxide.

4. The computer-accessible medium of claim 1, wherein the computer arrangement is configured to:

determine the functional brain age of the patient based on the PSD.

5. The computer-accessible medium of claim 4, wherein the computer arrangement is further configured to:

determine a normalized PSD (nPSD) based on the PSD; and determine the functional brain age of the patient based on the normalized PSD.

6. The computer-accessible medium of claim 5, wherein the computer arrangement is configured to determine the nPSD by dividing the PSD by a sum in a particular frequency range.

7. The computer-accessible medium of claim 6, wherein the particular frequency range is from about 0.4 Hz to about 30.5 Hz.

8. The computer-accessible medium of claim 5, wherein the computer arrangement is further configured to determine a spectral entropy of the nPSD.

9. The computer-accessible medium of claim 4, wherein the computer arrangement is further configured to determine at least one of (i) a power in a range of about 0.530 Hz based on the PSD, (ii) an alpha-band power based on the PSD, (iii) a beta-band power based on the PSD, (iv) a delta-band power based on the PSD, or (v) theta-band power based on the PSD.

10. The computer-accessible medium of claim 9, wherein (i) the alpha-band power is about 7.8-12.5 Hz, (ii) the beta-band power is about 12.5-25 Hz, (iii) the delta-band power is about 0.4-3.9 Hz, and (iv) the theta-band power is about 3.9-7.8 Hz.

11. The computer-accessible medium of claim 9, wherein the computer arrangement is configured to determine:

the alpha-band power by dividing a first sum of the PSD in a first range of about 8 Hz to about 12 Hz by a second sum of the PSD in a second range of about 0.4 Hz to about 30 Hz; and the beta-band power by dividing a third sum of the PSD in a third range of about 12 Hz to about 25 Hz by a fourth sum of the PSD in the second range.

12. The computer-accessible medium of claim 1, wherein the computer arrangement is further configured to decompose the PSD.

13. The computer-accessible medium of claim 12, wherein the computer arrangement is further configured to decompose the PSD into a periodic component and an aperiodic component in the EEG information.

14. The computer-accessible medium of claim 12, wherein the computer arrangement is further configured to fit the aperiodic component based on a broadband offset, a frequency vector, and a slope.

15. The computer-accessible medium of claim 1, wherein the EEG information includes EEG information from a frontal region of a brain of the patient.

16. The computer-accessible medium of claim 1, wherein the computer arrangement is further configured to apply an adaptive filtering procedure to the EEG information.

17. The computer-accessible medium of claim 16, wherein the computer arrangement is further configured to exclude edge effects cause by the adaptive filtering procedure.

18. A system for determining a functional brain age of a patient during an administration of a compound, comprising:

a computer hardware arrangement configured to:

receive electroencephalographic (EEG) information for a patient during the administration of the compound to the patient;

receive an entropy of the EEG information for the patient during the administration of the compound;

determine a functional brain age of the patient based on the entropy; and adjust the administration of the compound based on the determined functional brain age of the patient.

19. A method for determining a functional brain age of a patient during an administration of a compound, comprising:

receiving electroencephalographic (EEG) information for a patient during the administration of the compound to the patient;

receiving an entropy of the EEG information for the patient during the administration of the compound;

using a computer hardware arrangement, determining a functional brain age of the patient based on the entropy; and outputting information associated with the determined functional brain age for use in adjusting the administration of the compound; and administering the compound according to the determined functional brain age of the patient.

* * * * *